US011622556B2

(12) United States Patent
Eley

(10) Patent No.: US 11,622,556 B2
(45) Date of Patent: Apr. 11, 2023

(54) RE-OILED AND HYPER-OILED LECITHIN CARRIER VEHICLES

(71) Applicant: BIO-UP MIMETIC TECHNOLOGIES, INC., La Habra, CA (US)

(72) Inventor: Crispin G. S. Eley, Fullerton, CA (US)

(73) Assignee: BIO-UP MIMETIC TECHNOLOGIES, INC., Fullerton, CA (US)

( * ) Notice: Subject to any disclaimer, the term of this patent is extended or adjusted under 35 U.S.C. 154(b) by 246 days.

(21) Appl. No.: 16/093,127

(22) PCT Filed: Apr. 12, 2017

(86) PCT No.: PCT/US2017/027267
§ 371 (c)(1),
(2) Date: Oct. 11, 2018

(87) PCT Pub. No.: WO2017/180783
PCT Pub. Date: Oct. 19, 2017

(65) Prior Publication Data
US 2022/0071198 A1 Mar. 10, 2022

Related U.S. Application Data

(60) Provisional application No. 62/321,601, filed on Apr. 12, 2016.

(51) Int. Cl.
*A01N 25/04* (2006.01)
*A01N 63/10* (2020.01)
(Continued)

(52) U.S. Cl.
CPC .............. *A01N 25/04* (2013.01); *A01N 3/00* (2013.01); *A01N 37/14* (2013.01); *A01N 63/10* (2020.01);
(Continued)

(58) Field of Classification Search
CPC .......... A61K 25/04; A61K 8/14; A61K 9/127; A01N 25/04
See application file for complete search history.

(56) References Cited

U.S. PATENT DOCUMENTS

| 5,766,628 A | 6/1998 | Nuernberg | |
|---|---|---|---|
| 2011/0318406 A1* | 12/2011 | Eley | A23D 7/0053 426/654 |
| 2015/0182542 A1* | 7/2015 | Hodgson | A61K 9/10 424/400 |

FOREIGN PATENT DOCUMENTS

| CN | 1947720 A | 4/2007 |
|---|---|---|
| CN | 101342167 A | 1/2009 |

(Continued)

OTHER PUBLICATIONS

Database WPI, Week 2-00911, Thomson Scientific, London, GB; AN 2009-E24525, XP002795329, 3 pages.

(Continued)

*Primary Examiner* — Carlos A Azpuru
(74) *Attorney, Agent, or Firm* — Lewis Roca Rothgerber Christie LLP

(57) ABSTRACT

A liposome composition having a lipid bilayer membrane, made of a crude or de-oiled lecithin, at least one triglyceride, a non-triglyceride active agent, and conditioned water. The liposome composition may be utilized for purposes and treatments including increased plant growth, insecticide or insect repellant, inhibiting fruit decay, forensic labeling of plants, wound treatment, and cosmetic applications.

16 Claims, 23 Drawing Sheets

(51) Int. Cl.

| | | |
|---|---|---|
| *A01P 7/04* | (2006.01) | |
| *A01P 1/00* | (2006.01) | |
| *A01N 3/00* | (2006.01) | |
| *A01N 37/14* | (2006.01) | |
| *A01N 65/10* | (2009.01) | |
| *A01N 65/22* | (2009.01) | |

(52) U.S. Cl.
CPC ............. *A01N 65/10* (2013.01); *A01N 65/22* (2013.01); *A01P 1/00* (2021.08); *A01P 7/04* (2021.08)

(56) References Cited

FOREIGN PATENT DOCUMENTS

| CN | 102274183 A | 12/2011 |
|---|---|---|
| EP | 0557825 A2 | 9/1993 |
| RU | 2126676 C1 | 2/1999 |
| RU | 2290170 C1 | 12/2006 |
| RU | 2325165 C1 | 5/2008 |
| WO | WO2008155389 A2 | 12/2008 |

OTHER PUBLICATIONS

Database WPI, Week 201232, Thomson Scientific, London, GB; AN 2012-A22969, XP002795330, 5 pages.

Mugabe, Clement, et al., "Mechanism of Enhanced Activity of Liposome-Entrapped Aminoglycosides against Resistant Strains of Pseudomonas aeruginosa", Antimicrobial Agents and Chemotherapy, vol. 50, No. 6, (Jun. 1, 2006), pp. 2016-2022, XP055637159.

Extended European Search Report dated Nov. 8, 2019, issued in corresponding EP Application No. 17783082.5, 13 pages.

Budai, Livia et al.; "Liposomes for Topical Use: A Physico-Chemical Comparison of Vesicles Prepared from Egg or Soy Lecithin"; Scientia Pharmaceutica; 2013; 81; pp. 1151-1166.

\* cited by examiner

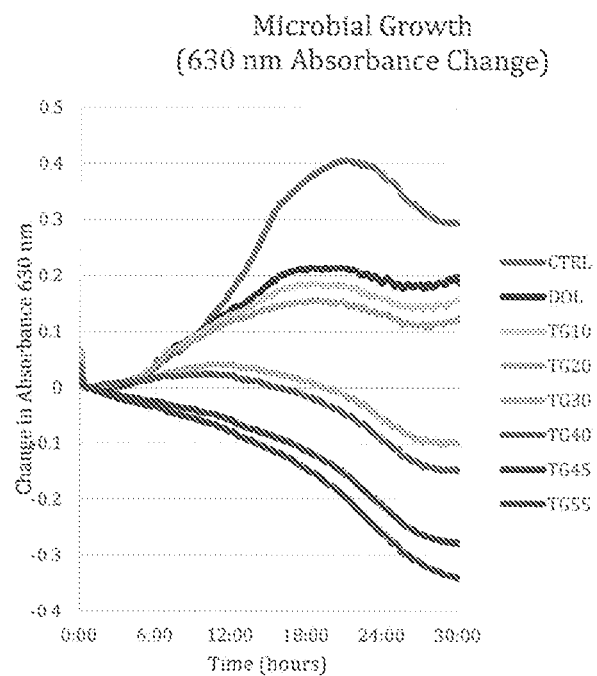
Figure 1(a) – Typical Growth Curves for *Sinorhizobium Meliloti*

Figure 1(b) – Magnitude of Growth Reduction (630 nm) vs. Triglyceride Content
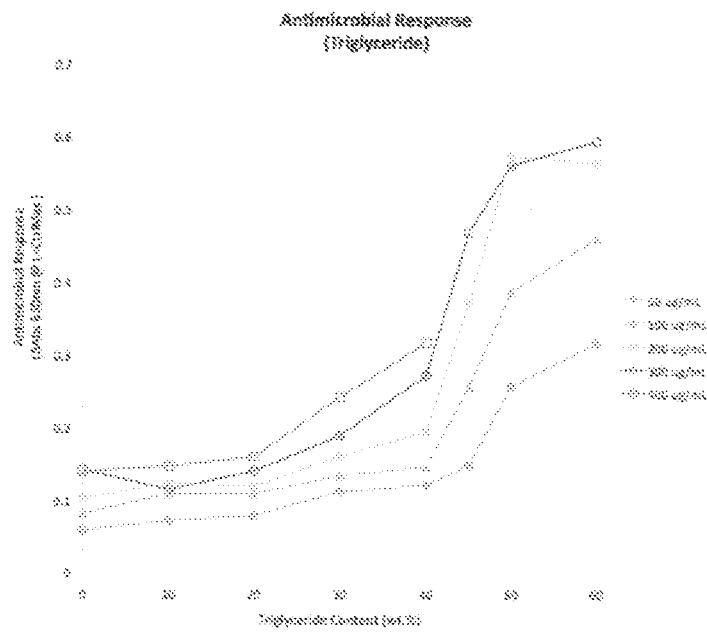
Figure 1(c) – Magnitude of Growth Reduction (630 nm) vs. Dose of Citronella EO
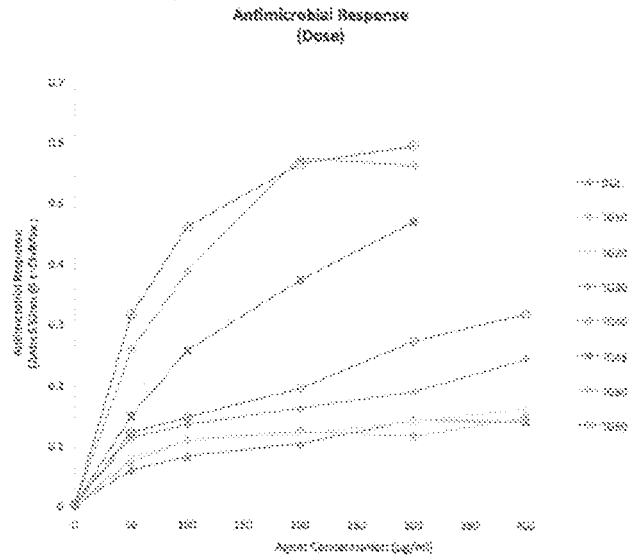

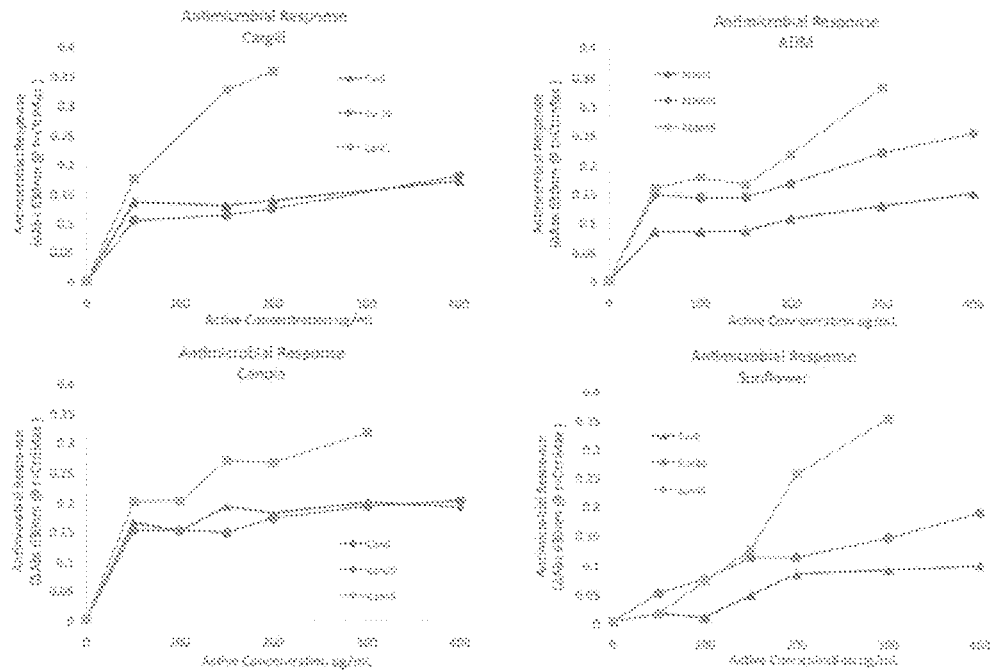
Figure 2(a) Alternative Lecithin Sources
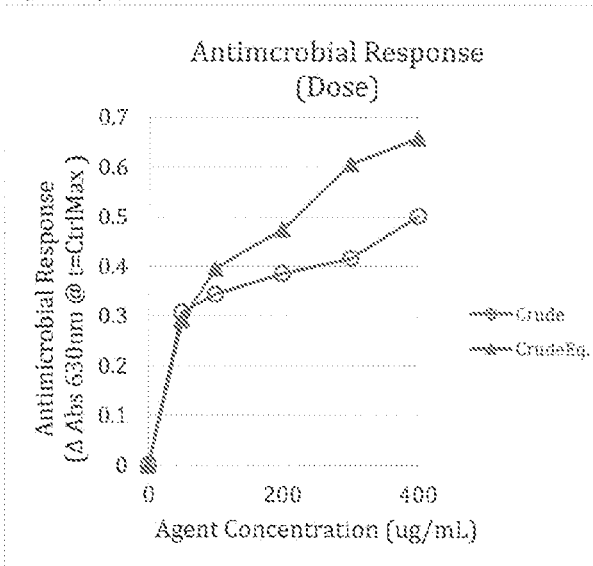
Figure 2(b) Re-Oiled vs Crude Lecithin

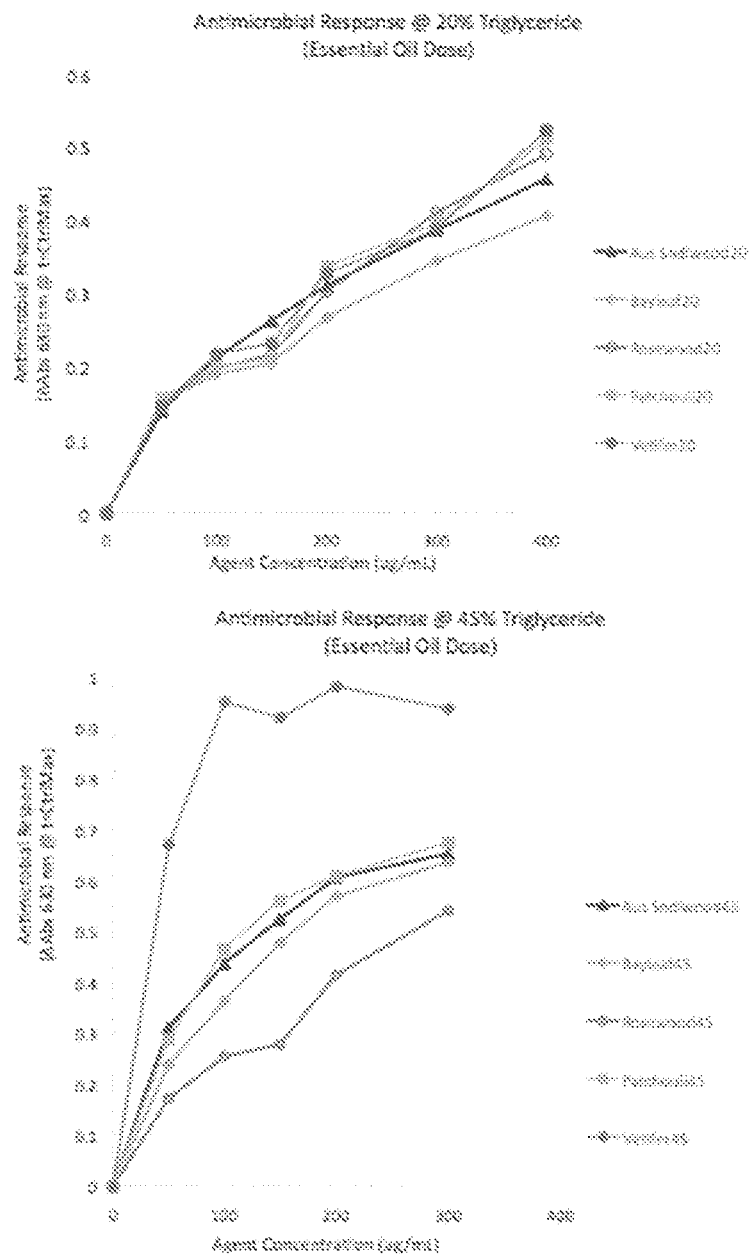

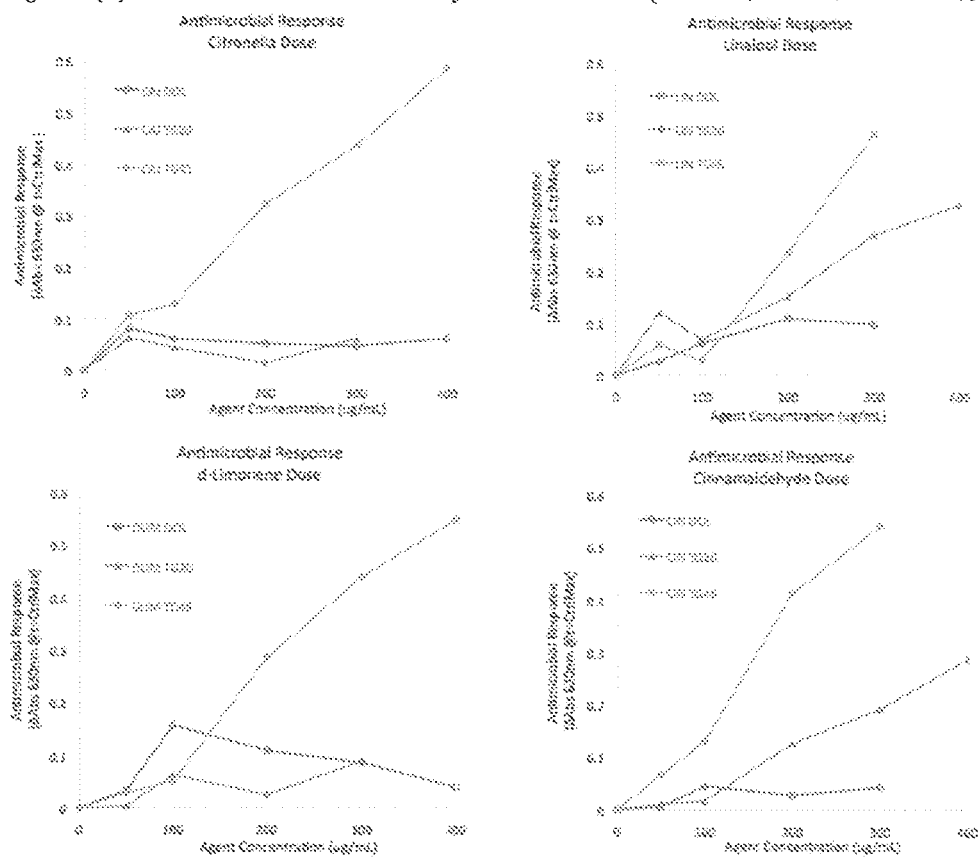

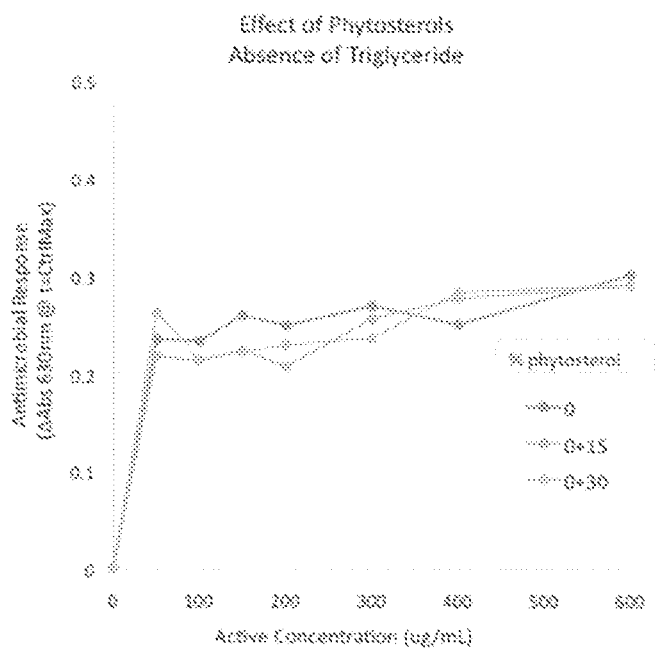
Figure 4 (a) Effect of Phytosterols in Absence of Triglyceride
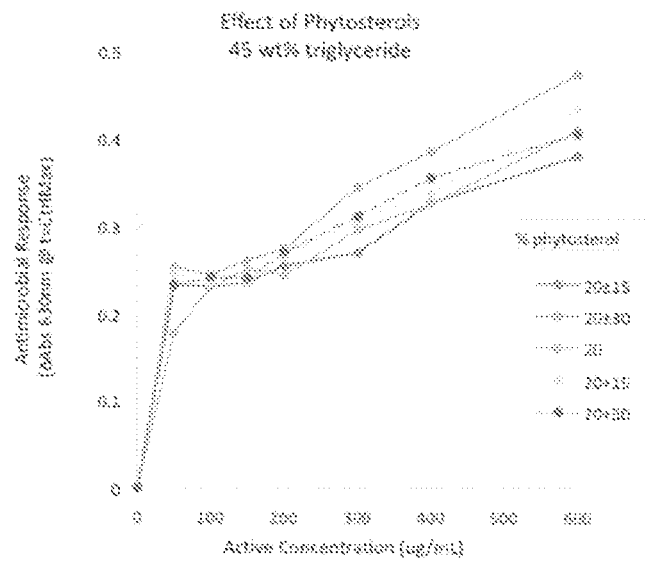
Figure 4(b) Effect of Phytosterols at High Triglyceride Content

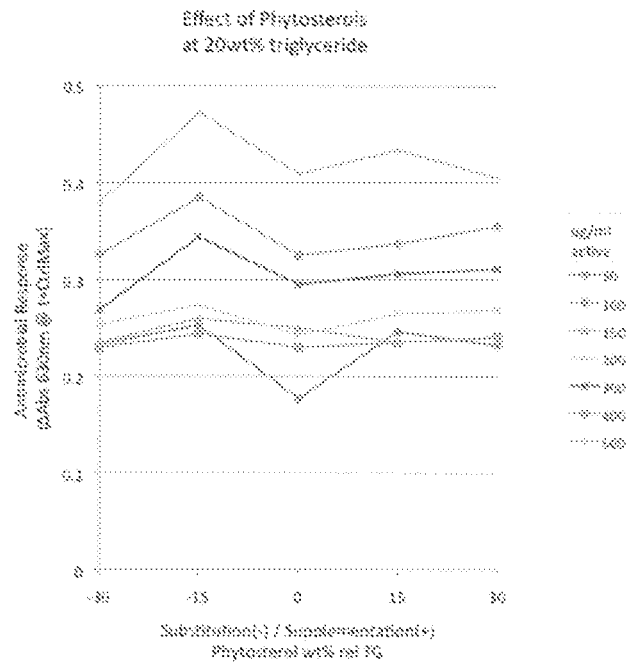

Figure 8(a)
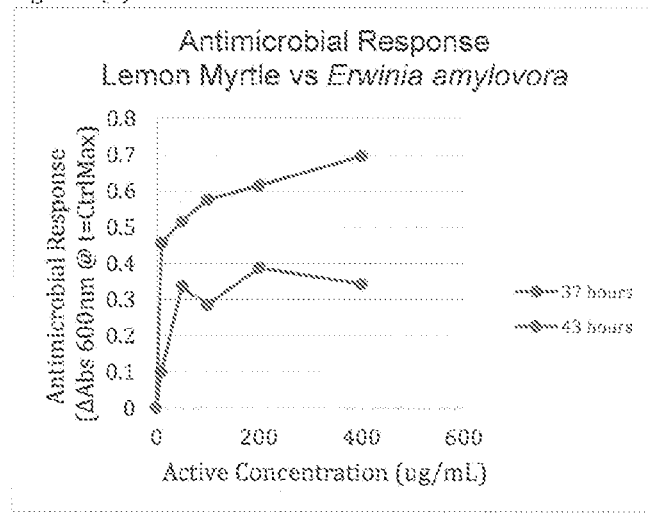
Figure 8(b) White Leaf Mold
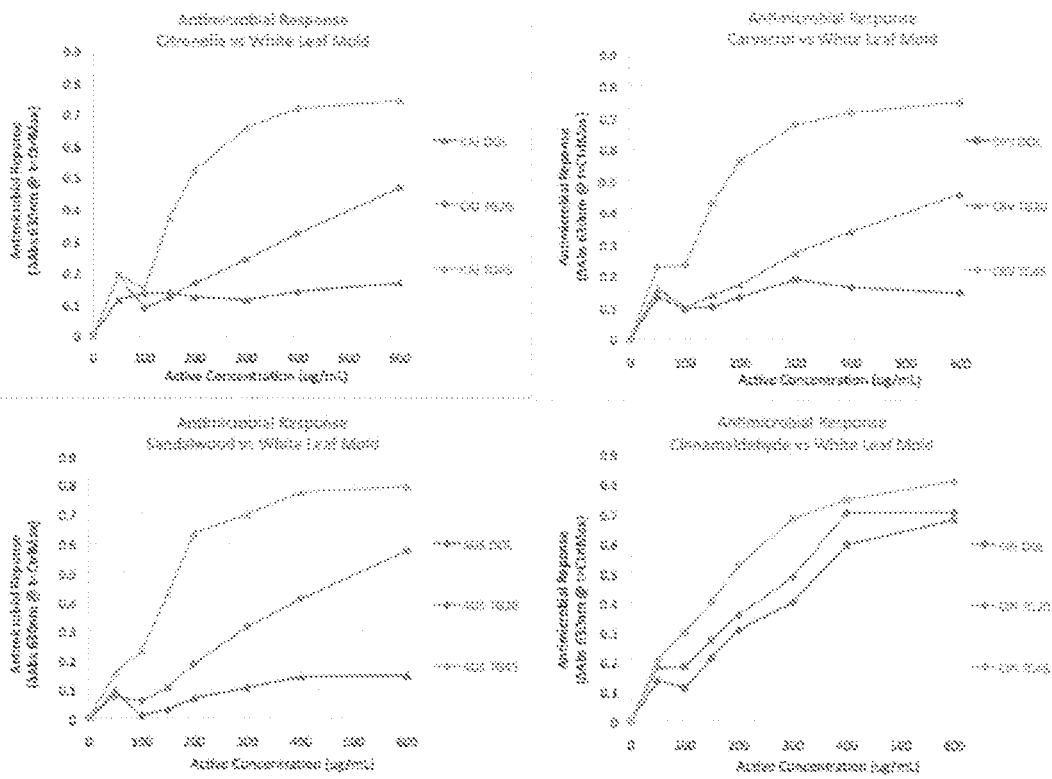

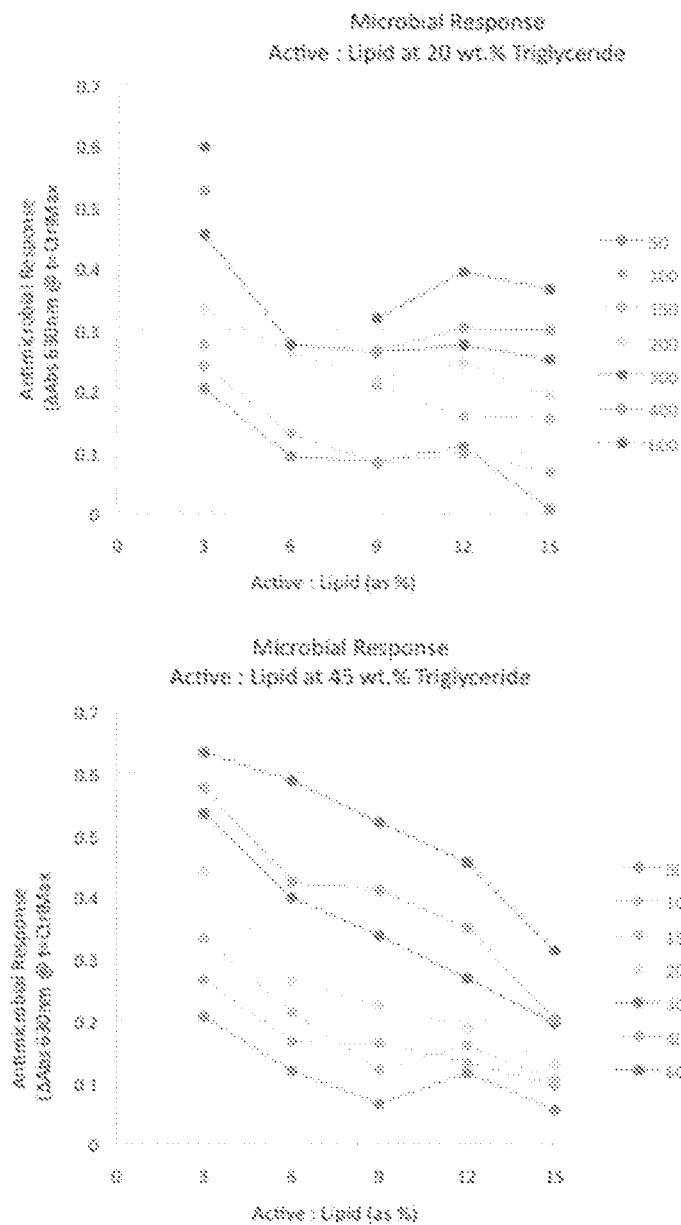
Figure 9(a) 3 – 15 wt.% Active

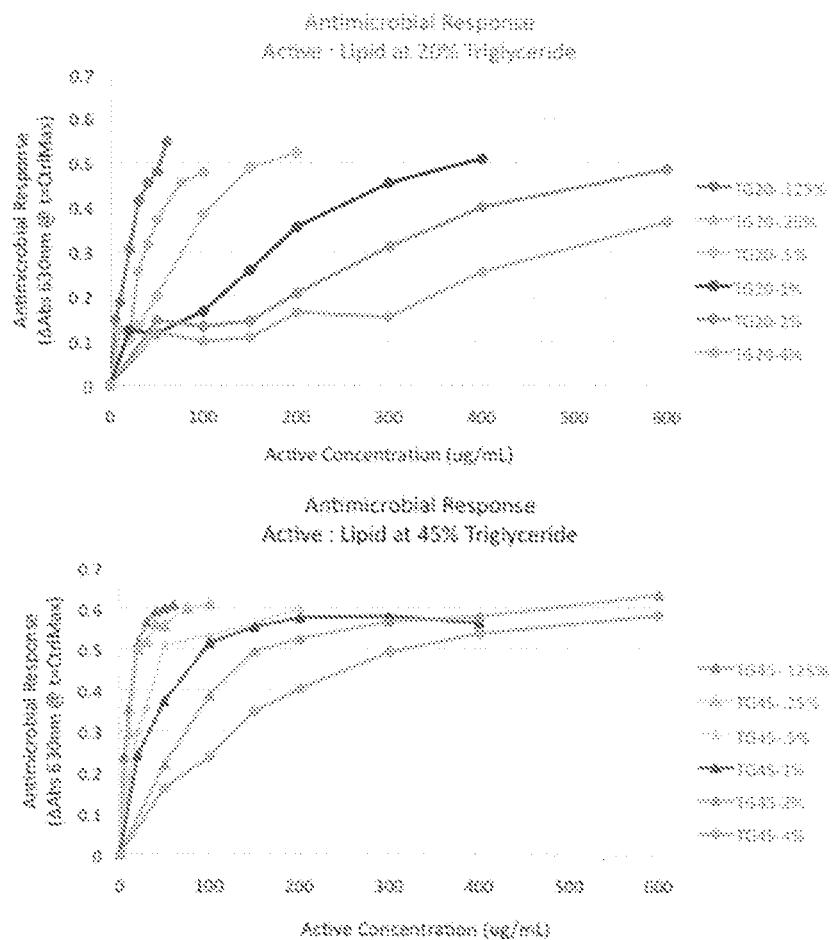

Figure 13(a) Leaf surface adhesion
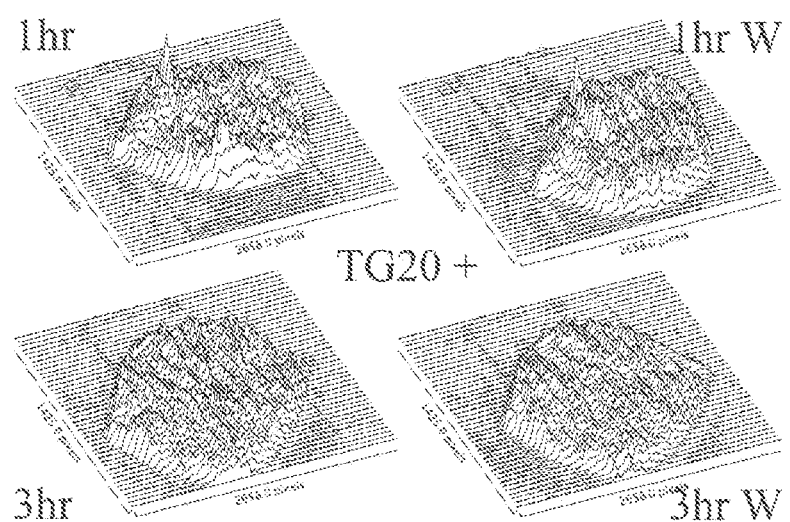
Liposomes prepared from de-oiled lecithin, with added 20% triglyceride, applied and left to dry on leaf surface for 1 or 3 hours. Fluorescence intensity plots from Image J: left images before washing, right images (W) after washing.

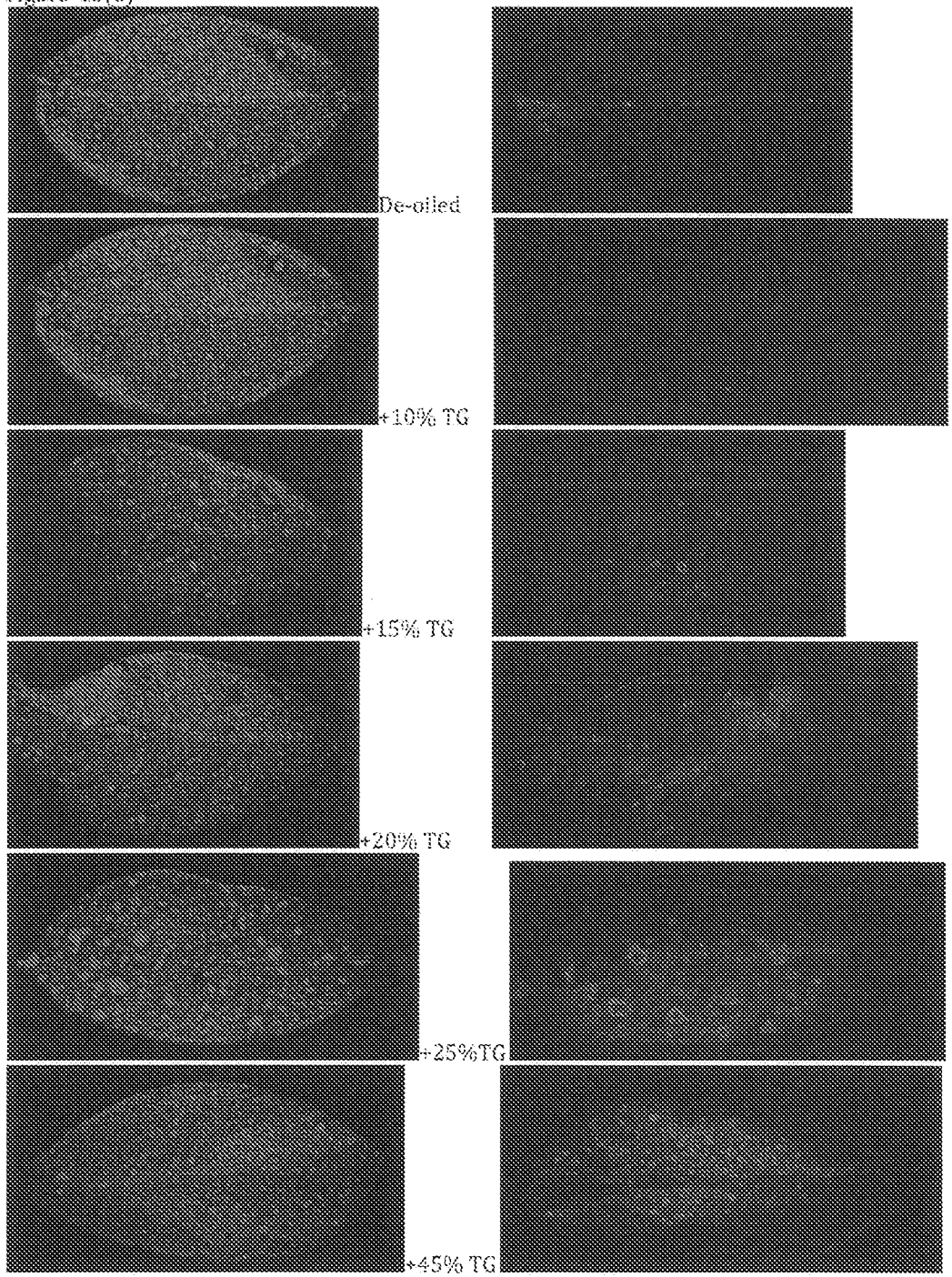

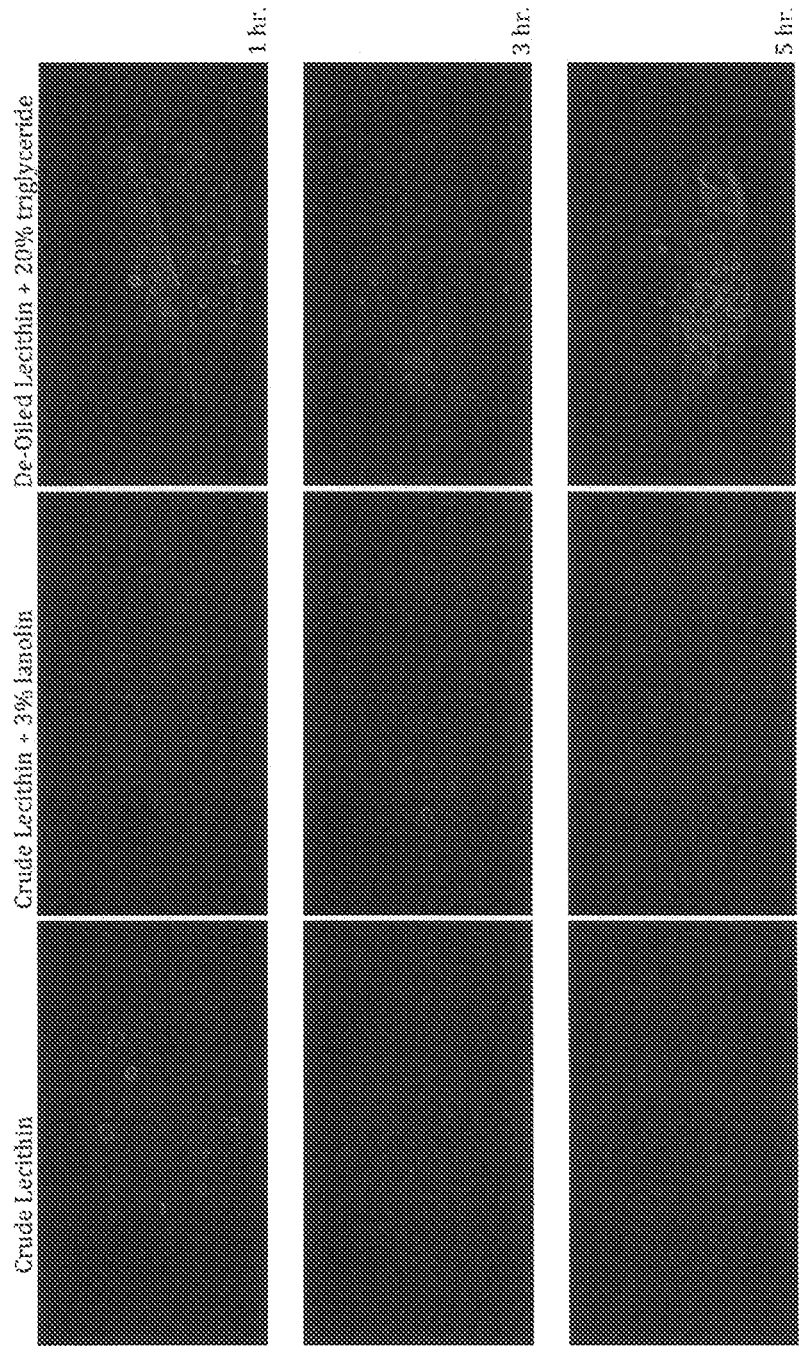

Figure 13(d)- Infected *pyrus kawakamii* leaf
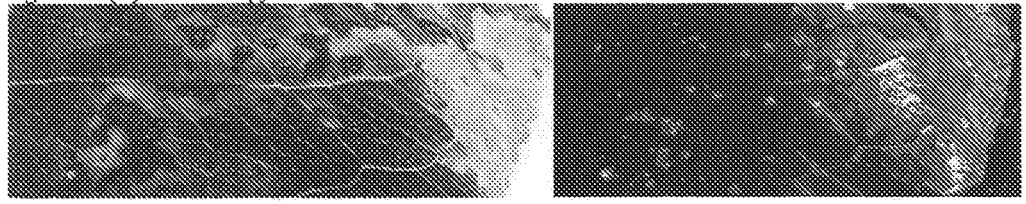
Figure 14(a) – Blueberry surface adhesion
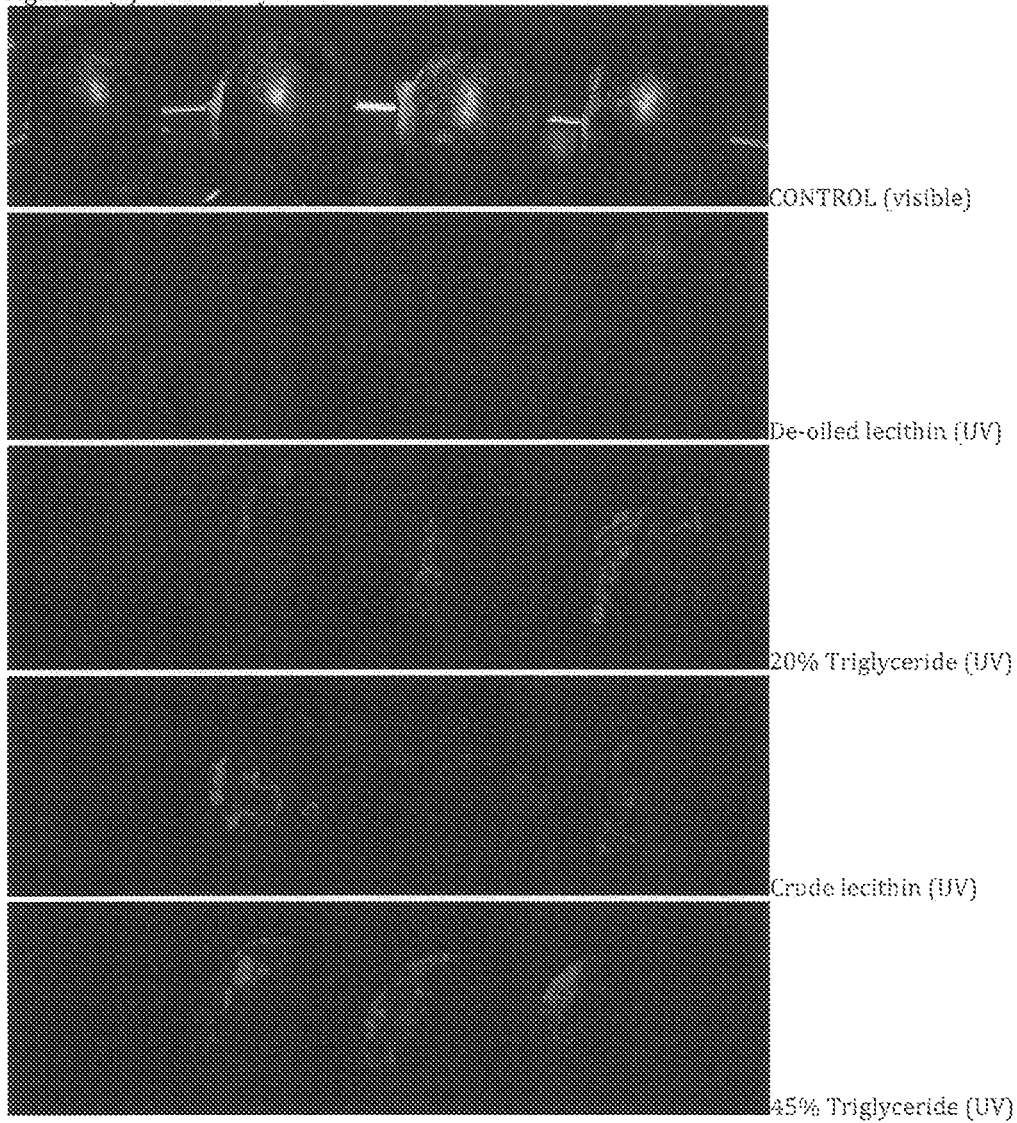

Figure 15 (a) "Kaplan Meyer plot" for *botrytis* infected strawberries
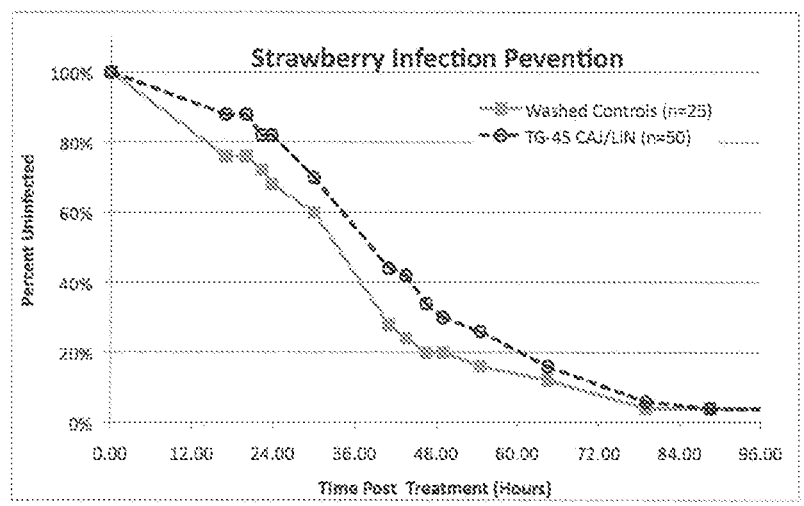
Figure 15 (b) Expanded plot
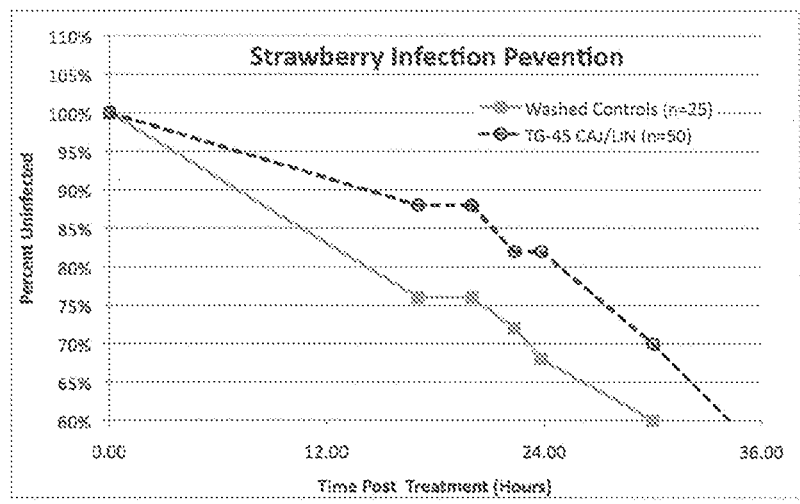

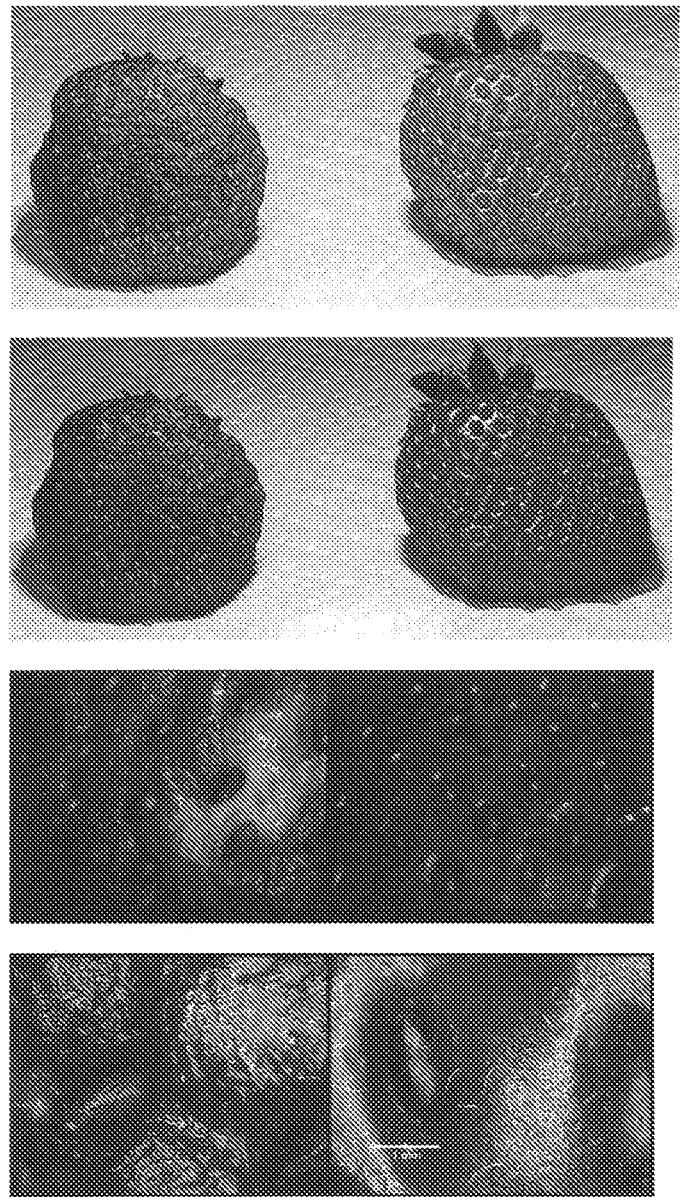

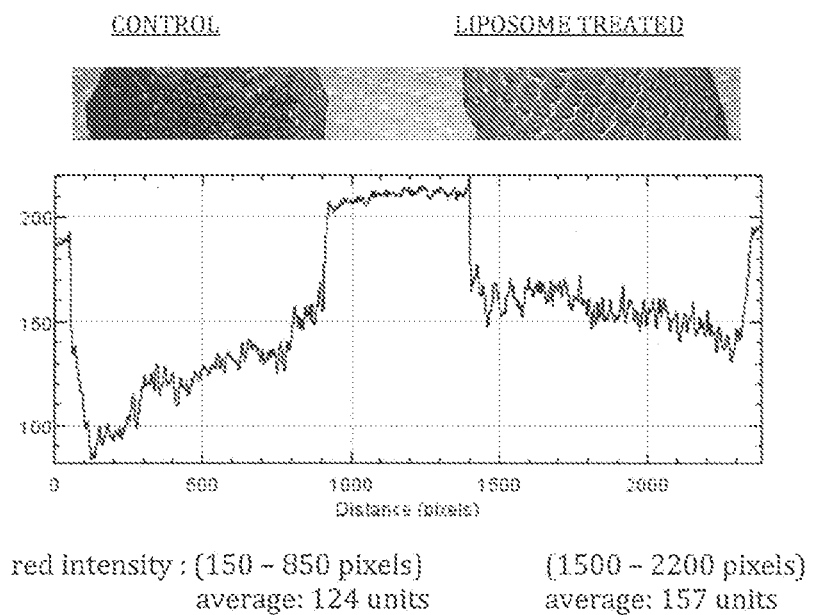

Figure 17 – Association of Fluorescence with Pond Water Particulate Matter
(a) visible light image of droplet  (b) uv illumination image
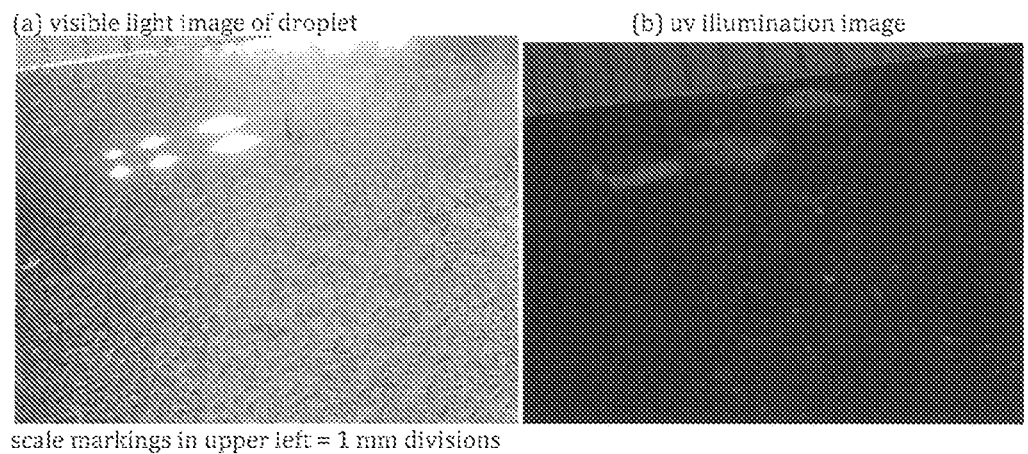
scale markings in upper left = 1 mm divisions
Figure 18 Mosquito larva
(a) visible light image
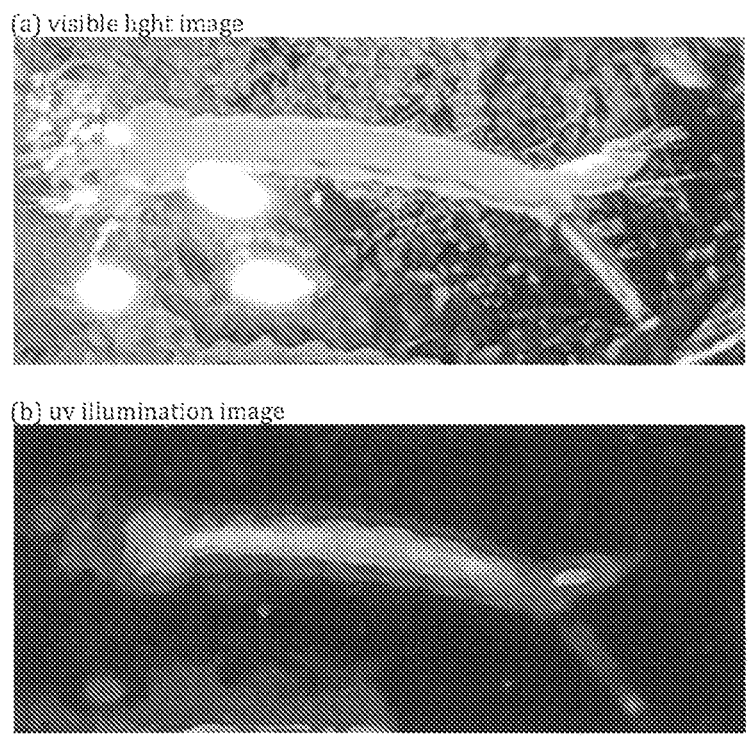
(b) uv illumination image

RE-OILED AND HYPER-OILED LECITHIN CARRIER VEHICLES

CROSS-REFERENCE TO RELATED APPLICATION(S)

This application is a National Phase Patent Application of International Patent Application Number PCT/US2017/027267, filed on Apr. 12, 2017, which claims priority to and the benefit of U.S. Provisional Application Ser. No. 62/321,601 filed on Apr. 12, 2016, entitled "Re-Oiled and Hyper-Oiled Lecithin Carrier Vehicles," the entire contents of which are both incorporated herein by reference.

TECHNICAL FIELD

This application is directed to lecithin carrier compositions and methods of making lecithin carrier compositions.

TECHNICAL BACKGROUND

The dispersion and stabilization of active ingredients may be desirable in order to store and manipulate these desired compounds in aqueous environments. Commonly used methods for dispersion have included emulsions, in which droplets of the active ingredient are dispersed and stabilized by a surfactant, or by milling or shearing of the desired compound into nanoparticles and dispersing the nanoparticles into a surfactant. However, these surfactant emulsions are often not stable, and the surfactant may be toxic or have undesired properties such as poor taste and/or the dispersion has cloudy appearance. These properties render these emulsions inadequate for dispersion of an active ingredient for consumption.

Phospholipids and other membrane-forming lipids are widely used to encapsulate active ingredients for transport in aqueous environments. In particular, phospholipid bilayer vesicles are formed when dried phospholipids are hydrated in aqueous solution, thereby generating concentric multiple phospholipid bilayers separated by aqueous compartments, known as multilamellar vesicles (MLVs). Phospholipids may also be manipulated to form unilamellar vesicles (UVs). These unilamellar vesicles together with the multilamellar vesicles can be categorized into three types—small unilamellar vesicles (SUVs) having a mean diameter in the range from 20 to 100 nm; large unilamellar vesicles (LUVs) having a mean diameter in the range from 150 to 1,000 nm; and multilamellar vesicles (MLVs) having a mean diameter in the range from 150 to 5,000 nm.

The phospholipid phosphatidylcholine (PC) is the basic component of commercial phospholipid vesicles, commonly with the addition of defined amounts of charged lipids such as phosphatidylglycerol. Lecithin is a mixture obtained from animal or plant sources by hydration of solvent-extracted oils that comprises acetone-insoluble phosphatides, the majority of which are phosphatidylcholine (PC), phosphatidylethanolamine (PE), and phosphatidylinositol (PI), combined with various amounts of other substances such as triglycerides, fatty acids, and carbohydrates.

Lecithin is a commonly used source of the phosphatidylcholine that is used in the preparation of phospholipid bilayers (Keller, B. C, 2001, Trends in Food Science Technology, 12, 25-31). Because the dispersion capabilities and stability of phospholipid vesicles has been shown to be dependent on the amount of phosphatidylcholine in the vesicles, high PC-content lipid mixtures (i.e., greater than 80% PC) are used for forming phospholipid vesicle carriers.

Although attempts have been made to use a lower PC-content to form dispersed liposomes for encapsulating a curcumin compound, those attempts did not result in dispersed vesicles encapsulating the curcumin. Takahashi et al. J. of Oleo Sci., 2007, 56, 35-42; (attempting to make liposomes having low-PC content) and Takahashi et al. J. of Agr. and Food Chem., 57, 9141-9146 (stating and proving that low-PC content liposomes did not work) are both incorporated by reference in their entirety.

In many protocols, the phosphatidylcholine is isolated from lecithin by de-oiling methods using acetone, followed by ethanol extraction, and a final liquid chromatography step to obtain high content phosphatidylcholine (i.e. greater than 80% PC of the total lipid content). To inhibit hydrolysis of the phospholipid vesicles, ionic buffers are used to control and maintain the pH of the vesicle environment (Vernooij, E., et al., Journal of Controlled Release, 2002, 79, 299-303). However, high PC-content lecithin is costly to make, and methodologies requiring certain organic solvents render the composition not desirable for human consumption. In this regard, there is a need for a phospholipid vesicle carrier that provides a stable dispersion of active ingredients using the fewest components and methods that do not require toxic solvents or expensive high-PC content lipid mixtures.

SUMMARY

A liposome composition having a lipid bilayer membrane comprises crude or de-oiled lecithin, at least one triglyceride, a non-triglyceride active agent, and conditioned water. The liposome composition wherein the non-triglyceride active agent is lipophilic and is incorporated in the lipid bilayer membrane. The liposome composition wherein the non-triglyceride active agent is membrane-impermeable and water soluble.

A dispersion of the liposome composition further comprising a surface-active agent.

The liposome composition further comprising lanolin, a lanolin derivative, a membrane-component sterol, or a non-triglyceride membrane lipid.

The liposome composition wherein the composition is subjected to a high shear method of size reduction.

The liposome composition wherein the volume weighted mean diameter as measured by dynamic light scattering is less than 1 micron.

The liposome composition wherein the volume weighted mean diameter as measured by dynamic light scattering is less than 500 nm and the liposomes are predominantly unilamellar.

The liposome composition wherein the weight ratio of added triglyceride to de-oiled lecithin is greater than about 1:5 and less than about 1.75:1.

The liposome composition wherein the weight ratio of added triglyceride to de-oiled lecithin is at least 1:1.5 and less than 1.5:1.

The liposome composition wherein the weight ratio of added triglyceride to crude lecithin is greater than about 0.05:1.

The liposome composition wherein the weight ratio of added triglyceride to crude lecithin is less than about 0.35:1.

The liposome composition wherein the ratio of moles of any lipophilic active agent to the sum of the moles of lecithin and any added triglyceride is selected from less than 1:1, more than 2:100 and no more than 80:100, or more than 10:100 and no more than 50:100.

The liposome composition further comprising up to 15 weight %, between 3% and 13 weight %, or between 3% and 8 weight % relative to de-oiled lecithin, of lanolin or a lanolin derivative.

The liposome composition further comprising up to 30 weight %, between 1 weight % and 20 weight %, or between 2 weight % and 10 weight %, of a natural membrane component sterol relative to the sum of the weights of lecithin and any added triglyceride.

A method of treating, inhibiting, or preventing bacterial, fungal or viral disease of plants, including fruit and seed thereof, before and after harvest, using the liposome composition.

A method of repelling pests using the liposome composition.

A method of killing insects at any stage of development using the liposome composition.

A method of inhibiting decay or preserving the appetizing appearance of fruit by using the liposome composition.

The method wherein the liposome composition is applied or sprayed on a plant of the fruit, the fruit, or a seed of the fruit.

The method wherein the liposome composition is injected into the plant.

The method wherein the liposome composition is applied to a root of the plant in soil or in water proximal to the plant.

The liposome composition wherein the active agent is a fluorescent molecule having an excitation wavelength in the ultraviolet region of the spectrum and an emission wavelength approximately corresponding to the excitation wavelength of a chlorophyll molecule.

The liposome composition wherein the fluorescent active agent is safe for human consumption in food, and/or during plant growth and or post-harvest processing the fluorescent active agent degrades to breakdown products that are safe for human consumption.

A method of increasing a plant's intake of solar or other source of visible or ultraviolet radiation by applying the liposome composition to the plant.

The liposome composition further comprising an added purified phospholipid or fatty acid.

The method wherein the liposome composition further comprises an added purified phospholipid or fatty acid.

The method or liposome composition wherein the liposome composition further comprises or is dispersed in an aqueous solution containing a surface active agent.

The method or liposome composition wherein the surface active agent is a polyoxyethylenesorbitanmonoalkylester or a polyoxyethylenealkylether.

A method of labeling a plant for forensic and other tracking purposes or for decorative purposes, the method comprising injecting the plant with the liposome composition wherein the liposome composition further comprises at least one colored or fluorescent dye, and if more than one dye wherein the dyes are in known proportion to one another.

A lotion, cream, or aqueous dispersion suitable for topical use prepared from the liposome composition.

The liposome composition wherein the liposome composition contains a compound or combination of compounds that is antimicrobial, analgesic, anti-inflammatory, antifungal, anti-parasitic or antiviral, or has a combination of these therapeutic properties.

A method of treating skin wound or injury in an animal, comprising applying the liposome composition by irrigation or spray.

A method of treating cosmetic blemishes, comprising the liposome composition.

A composition comprising the foam produced from the liposome composition comprising admixing gas to the liposome composition.

A method of treating or washing a body cavity by irrigating or rinsing with the liposome composition.

A method of reducing or eliminating the resistance of microbes to an antimicrobial agent, comprising contacting the microbes with the liposome composition. The method wherein the lecithin used to prepare the liposome composition has a phosphatidylcholine content greater than 80 percent by weight. The method wherein the liposome composition is an adjuvant to a non-liposomal antimicrobial agent. The method wherein the liposome composition does not contain a non-triglyceride anti-microbial agent.

BRIEF DESCRIPTION OF THE DRAWINGS

FIG. 1(a) is a graph showing microbial growth for *Sinorhizobium meliloti*, according to embodiments of the present invention.

FIG. 1(b) is a graph showing antimicrobial response using de-oiled lecithin with increasing amounts of triglyceride content, according to embodiments of the present invention.

FIG. 1(c) is a graph showing antimicrobial responses using de-oiled lecithin with increasing amounts of citronella, according to embodiments of the present invention.

FIG. 2(a) shows four graphs measuring antimicrobial response, with each graph showing the antimicrobial response for a different plant source of lecithin and/or method of de-oiling, according to some embodiments of the present invention.

FIG. 2(b) is a graph of showing antimicrobial response for de-oiled lecithin and crude lecithin, according to embodiments of the present invention.

FIG. 3(a) shows graphs of relative antimicrobial activity of essential oils (sandlewood oil shown in red, bayleaf oil shown in green, rosewood oil shown in blue, patchouli oil shown in orange, and vetiver oil shown in brown) with 20% triglyceride by weight or 45% triglyceride by weight as indicated, according to some embodiments of the present invention.

FIG. 3(b) shows graphs of relative antimicrobial activity of de-oiled lecithin liposomes in de-oiled lecithin (DOL) alone (shown in blue), de-oiled lecithin with 20% triglyceride by weight (shown in orange) or de-oiled lecithin with 45% triglyceride by weight (shown in green), as indicated, according to embodiments of the present invention.

FIG. 4(a) is a graph showing the antimicrobial effect of de-oiled lecithin liposomes made with phytosterols in the absence of triglycerides, with de-oiled lecithin (DOL) alone (0) shown in blue, DOL with 15% phytosterol by weight shown in orange, and DOL with 30% phytosterol by weight shown in gray, as indicated, according to embodiments of the present invention.

FIG. 4(b) is a graph showing the antimicrobial effect of phytosterols at high triglyceride content (45% triglyceride by weight) with the amounts of phytosterol and de-oiled lecithin as indicated, according to embodiments of the present invention.

FIG. 4(c) is a graph showing the antimicrobial effect of phytosterols at intermediate triglyceride content as indicated, according to embodiments of the present invention.

FIG. 5(a) is a graph showing the antimicrobial effect of de-oiled liposomes made with 0% lanolin (gray), 1% lanolin (blue), and 8% lanolin (orange), according to embodiments of the present invention.

FIG. 8(a) is a graph showing the antimicrobial response of liposomes made with de-oiled lecithin and lemon myrtle oil on the bacterium, *Erwinia amylovora*, after incubation at 37 hours (blue) or 43 hours (red), as indicated, according to embodiments of the present invention.

FIG. 8(b) shows graphs depicting the antimicrobial response of liposomes made with de-oiled lecithin and citronella oil, carvacrol oil, sandalwood oil, or cinnamaldehyde oil on white leaf mold, with DOL liposomes of each oil without triglycerides (DOL shown in blue), with 20% triglycerides by weight (TG20 shown in orange), or with 45% triglycerides by weight (TG45 shown in green), as indicated, according to embodiments of the present invention.

FIG. 9(a) shows graphs depicting the antimicrobial response of de-oiled lecithin liposomes made with 20% triglyceride by weight (upper graph) or 45% triglyceride by weight (lower graph) as function of 3, 6, 9, 12 or 15% active ingredient (citronella java), as indicated, according to embodiments of the present invention.

FIG. 9(b) shows graphs depicting the antimicrobial response of de-oiled lecithin liposomes made with 20% triglyceride by weight (upper graph) or 45% triglyceride by weight (lower graph) as a function of the amount of the active ingredient (citronella java) from 0.125% to 4% by weight, as indicated, according to some embodiments of the present invention.

FIG. 13(a) shows fluorescence intensity plots of leaf surface adhesion of *Citrofortunella microcarpa* leaves at 1 and 3 hours after being sprayed with liposomes made of de-oiled lecithin, DFSB, and 20% triglyceride by weight, and after washing, as indicated, according to embodiments of the present invention.

FIG. 13(b) shows UV illumination of *Citrofortunella microcarpa* leaves sprayed with liposomes made of de-oiled lecithin, DFSB, and 0, 10, 15, 20, 25, or 45% triglyceride by weight, as indicated, before (left image) and after (right image) washing, as indicated, according to embodiments of the present invention.

FIG. 13(c) shows UV illumination of *Citrofortunella microcarpa* leaves that were washed after being sprayed with liposomes with DFSB, the liposomes made of crude lecithin, crude lecithin with 3% lanolin, or de-oiled lecithin, as indicated, according to embodiments of the present invention.

FIG. 13(d) shows visible (left) and UV (right) light images of *Pyrus kawakamii* leaves with a leaf rust infection after treatment with a pump aerosol spray of a dispersion of DFSB fluorescent-labeled liposomes (de-oiled lecithin with 20% triglyceride) and allowed to dry for 48 hours, according to embodiments of the present invention.

FIG. 14(a) shows light or UV illumination images of blueberries after a spray treatment of DFSB-labeled liposomes made with de-oiled lecithin, de-oiled lecithin with 20% triglyceride by weight, crude lecithin, or de-oiled lecithin with 45% tricglyceride by weight, as indicated, according to embodiments of the present invention.

FIG. 15(a) is Kaplan Meyer plot of "uninfected" strawberries after all strawberries were injected with *botrytis*, the plot comparing the percent of uninfected strawberries of those that were washed in water (controls) or with a wash of liposomes made with de-oiled lecithin, 45% triglyceride by weight and citral or linalool, as indicated, according to embodiments of the present invention.

FIG. 15(b) is an expanded-scale panel of the plot shown in FIG. 15(a).

FIG. 16(a) shows color and grayscale images of a matched pair of strawberries taken after 48 hours at ambient temperature with the control and liposome-treated strawberries being injected and washed as described in FIG. 15(a).

FIG. 16(b) shows a color image of the pair of strawberries in FIG. 15(a) and the corresponding red channel analysis of the color image, according to embodiments of the present invention.

FIGS. 17(a)-17(b) show visible light (FIG. 17(a)) and UV illumination (FIG. 17(b)) images showing adherence of DFSB-labeled liposomes to particulate matter in pond water, for which the DFSB-labeled liposomes are made with 0.0015% by weight DFSB, de-oiled lecithin, 20% triglyceride by weight, and coriander and lavender oils each at 2.5% by weight, according to embodiments of the present invention.

FIGS. 18(a)-18(b) show visible light (FIG. 18(a)) and UV illumination (FIG. 18(b)) images showing adherence and distribution of DFSB-labeled liposomes within a mosquito larva, for which the DFSB-labeled liposomes are made with 0.0015% by weight DFSB, de-oiled lecithin, 20% triglyceride by weight, and coriander and lavender oils each at 2.5% by weight, according to embodiments of the present invention.

DETAILED DESCRIPTION

Figure 5B:
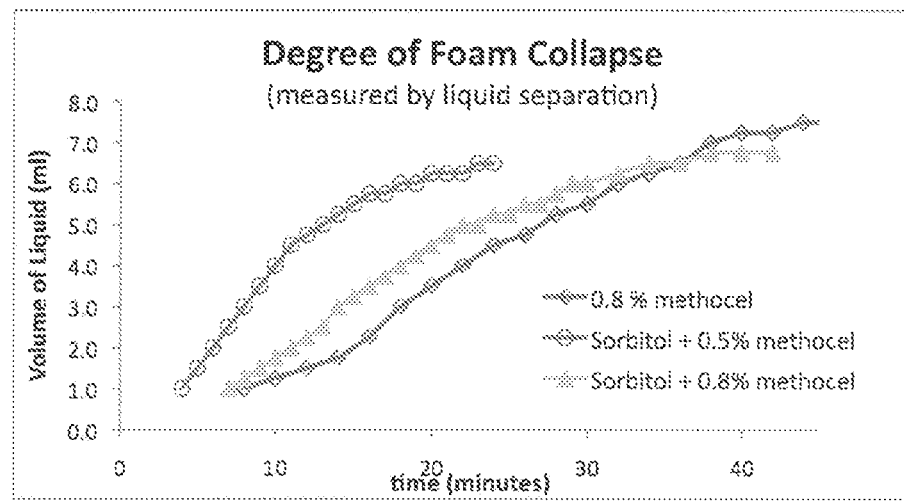
FIG. 5(b) is a graph showing the degree of foam collapse as measured by liquid separation of foam made with de-oiled lecithin with: 0.8% carboxymethylcellulose (methocel) as shown in blue, sorbitol and 0.5% methocel as shown in red, or sorbitol and 0.8% methocel as shown in green, according to embodiments of the present invention.

The present invention is directed to formulations of active agents in liposomes that are prepared from de-oiled lecithin to which one or more triglycerides have been added to "re-oil" the lecithin or from crude lecithin to which one or more triglycerides have been added to "hyper-oil" the lecithin (to a triglyceride content above the level naturally present in the crude lecithin). Lecithin is defined in this invention as a complex mixture obtained from animal and plant sources by hydration of solvent-extract oils, as defined in the *Joint World Health Organization/United Nations Food Safety Agency Evaluation, Committee for Food Additives (JECFA)*. (Food and Agriculture Organization of the United Nations, Food and Nutrition Paper 52, "Compendium of Food Additive Specifications" (FNP 52), Addendum 2 (1993)), that is incorporated by reference in its entirety. This complex mixture, considered herein as "crude lecithin", comprises acetone-insoluble phosphatides including predominantly phosphatidylcholine, phosphatidylethanolamine, and phosphatidylinositol, as well as smaller amounts of triglycerides, fatty acids, and carbohydrates. Further, de-oiled lecithin is the acetone-insoluble fraction of this mixture from which the plant triglycerides and certain other minor components have largely been removed, for example by ultrafiltration or an acetone precipitation process. The invention contemplates the use of crude lecithin from any sources, especially such common crops as soybeans, canola and sunflower, as well as de-oiled forms of lecithin prepared by differing methods such as ultrafiltration or acetone precipitation.

Re-oiled lecithin, as the term is used herein, comprises de-oiled lecithin to which one or more triglycerides have been added, (at a level either equal to, lower or higher than the amount of triglyceride present in the crude lecithin from which the de-oiled material was prepared). Relative to crude lecithin, this re-oiled lecithin is substantially reduced in certain minor non-triglyceride components of crude lecithin such as sterols and free fatty acids. Hyper-oiled lecithin comprises crude lecithin, (that is, a mixture of phosphatides and triglycerides as well as non-phosphatide, non-triglyceride components), and further triglycerides added to enrich the lecithin in triglycerides to a level above that found in the crude lecithin.

In particular, the amount of triglyceride is adjusted to provide for particular performance in the antimicrobial and antiviral activity of the liposome and delivery of added associated active agent, especially when said agent is lipophilic and incorporated in the bilayer membrane of the liposome. In suitable formulations, the triglycerides themselves—as delivered by liposomes—have antimicrobial activity. In this context "incorporated in" has the conventional meaning of "being a part of" and is intended to exclude active agents either in the encapsulated aqueous portion or portions of the liposomes or bound to the surface of the liposome membranes. The specific triglyceride or triglyceride mixture can also be tuned to adjust the rate (and duration), extent, and mechanism of delivery of the active agent. It can also be tuned for optimum activity of the triglycerides themselves against pathogens when delivered in liposomes, or for best performance of the liposomes in protecting or preserving the outer tissue layers of living organisms. Of particular utility are the plant oil triglycerides commonly used as cooking oils such as corn, sunflower, safflower, olive, grape seed, soybean, canola and coconut oils, and more highly purified long and medium chain triglycerides generally. It is further contemplated that incorporation of another membrane lipid component, such as a sterol, as an alternative or addition to the triglyceride or triglycerides, can be used for such tuning. In addition, the incorporation of lanolin, or lanolin derivatives, provides a similar ability for tuning to that provided by sterols. As well as tuning by adjustment of the content of triglyceride and other membrane lipid components such as sterols (and lanolin), the performance tuning can be further enhanced by altering the weight and thus molar ratio of active agent(s) to the other liposome components.

Without wishing to be bound by a particular theory, the plant oil triglycerides, membrane component sterols, and lanolin or lanolin derivatives, are expected to change the hydrophilic/hydrophobic balance of the surface profile of the liposomes containing the active agent. There is a known "umbrella" effect of phospholipids, whereby the hydrophilic phospholipid head groups can shield or cover more hydrophobic portions of other membrane components that are exposed at or near the liposome bilayer surface. Increasing the proportion of these other membrane components alters the fraction of the surface that can be "umbrella" covered by the phospholipids. The resulting change in liposome surface characteristic is postulated to change the interaction of the liposomes with, for example, proteins, including bacterial exo-enzymes, cells such as fungi and bacteria, viral particles, and surfaces generally, including plant surfaces. As a non-limiting example, fusion of liposomes with, or endocytosis by, cells can be facilitated by an appropriate hydrophilic/hydrophobic balance of the surface profile (created by adjusting triglyceride content).

The delivery by this method of triglycerides alone, in the absence of added active agent, can have a deleterious, even lethal effect on the pathogenic cells. We speculate that the membrane structural changes associated with the triglycerides in the liposome bilayer are repeated to some degree in the membrane of the target organism. It is known from human disease pathology that formation of high triglyceride content domains can compromise cell function. The modulation of target cell membrane fluidity also has the potential to enhance the activity of a co-delivered lipophilic active agent, or of such an agent, or other anti-pathogenic agent of any class, delivered independently. Such an effect is very desirable for activity against drug resistant pathogens (e.g. MDR-TB), some of which have cell membranes with unusually low fluidity that is believed to be a significant factor in the resistance.

It is important to note that the charge density on the liposome surface, commonly assessed by zeta-potential measurements, represents only one element of the hydrophilic/hydrophobic balance of the surface profile. The headgroup size, and therefore "reach" of the umbrella effect, of neutral phospholipids such as phosphatidylcholine is clearly a factor that is not captured by zeta potential. By way of illustration, consider the theoretical example of a neutral liposome prepared from pure phosphatidylcholine; the zeta potential remains at zero (at neutral pH) even on addition to the liposome membrane of triglyceride that alters the hydrophilic/hydrophobic balance of the surface profile.

To the extent that the plant oil triglycerides, membrane component sterols and lanolin, or lanolin derivatives, pack differently in the liposome membrane, that differential packing then has a modulating effect on the hydrophilic/hydrophobic balance of the surface profile of the liposomes. Thus highly saturated short chain triglycerides from coconut oil pack differently from long chain unsaturated triglycerides such as olive oil which in turn are clearly different from phytosterols and lanolin in structure, and therefore in packing intercalation with the phospholipids. It is anticipated that there are also specific surface chemistry interaction effects that vary with the nature of the triglyceride, sterol or lanolin components.

This invention, however, does not contemplate altering the composition of liposome membranes to optimize the release through the membrane of membrane-permeable water-soluble agents from the aqueous interior compartment of the liposome, an effect that others have shown for relatively low levels of triglyceride in purified phosphatidylcholine membranes. The compositions of this invention may, none-the-less, be optimized for liposomal delivery of membrane impermeable water-soluble active agents by changing the way the target tissues (cells, plant surfaces etc) interact with the liposome surface rather than changing the release of the water-soluble active agents from the liposome by leakage through the membrane.

The use of polysorbates (polyoxyethylenesorbitan monoalkylesters), polyoxyethylene alkyethers (POE) or other common surface-active agents as additional components of liposome preparations or dispersions is also contemplated. These surface-active agents may be included to further modify the properties of the liposome preparations, by altering either the properties of the liposomes or the surface wetting characteristics of the liposome dispersions, with the goal of tuning the active agent delivery. The agents may be present as components of the liposomes themselves or as adjuvants to pre-formed liposomes in aqueous dispersions. In this latter case, the composition of the liposomes is selected to ensure that they are stable in the presence of adjuvant added after the preparation of the liposome dispersion.

This invention has particular utility for the delivery of lipophilic active agents. It has surprisingly been discovered that tuning the triglyceride content allows the effective delivery of active agents, in particular lipophilic active agents, to plant pathogens such as bacteria and fungi. This delivery inhibits the activity of the pathogen either by inhibiting growth or killing the organism. At certain levels of triglyceride content, and for certain pathogens, the triglyceride itself provides inhibitory activity that is enhanced when lipophilic active agents are added. Similar effective delivery to viral pathogens is expected. The formulations, some made with inexpensive natural materials, are of great utility in treating crop diseases. Other areas of application will be obvious to those skilled in the art, for example in the delivery of suitable active agents to the skin, nail, hoof or mucosa—including compromised, burned or otherwise wounded areas—of an animal. For certain compositions an injectable presentation is contemplated for use in the treatment in animals of viral, fungal, bacterial, parasitic or spongiform encephalopy infections. A further contemplated application is to feed or water for animals to consume for the purpose of supporting animal health and improving feed-conversion ratios, for example by altering the intestinal microbial population of the animals. Yet another use for the liposomes of the present invention, for which the composition may be optimized, is reduction in the deleterious effect of pond microorganisms on aquaculture by controlling the number and/or growth rate of these microorganisms. The active agents may be synthetic or naturally occurring molecules having the desired activity upon delivery—they include synthetic and natural antibacterial, antifungal and antiviral molecules as well as natural agents that have one or more of these properties, for example the isolated, or mixed, essential oils such as carvacrol, eucalyptol, oil of thyme, tea tree oil, cinnamaldehyde etc. The activity may be enhanced relative to the known activity of the free (non-liposomal) active agent, or may only become apparent by virtue of the use of the present invention. Furthermore, by modulating the delivery of these agents through the use of the carriers of this invention, previously unobserved or unobtainable synergies of activity of the selected agents, with each other or with triglycerides, become achievable.

It has also been determined that the formulations of the present invention can be tuned to optimize the biodistribution within and on plants, including fruit, both to allow for effective antimicrobial (bacterial and fungal) and antiviral treatments and to facilitate an optimized delivery within and on plants of pesticidal and pest-repellent agents. A further utility of certain of the liposomal formulations is their ability to preserve harvested fruit against drying out and/or post-harvest infection. The formulations may be optimized to be stable in the presence of adjuvant surface-active agents, for example those used to ensure even leaf coverage or stomatal flooding, while retaining an optimized desired activity for the active agent. This tuning of surface distribution is distinct from the use of empty (non active containing) liposomes for the purpose of changing wetting characteristics of solutions of water-soluble non-liposomal active agents in which pre-formed liposomes are mixed.

The de-oiled lecithin contemplated by this invention may have been further purified to enrich the content of phosphatidylcholine, but, in preferred embodiments, the resulting phosphatidylcholine-enriched lecithin is not ethanol soluble. In most embodiments, the composition of the homogeneous mixture from which the liposomes are prepared, see examples, has lecithin as the component present in the largest amount by weight. In certain embodiments, the triglyceride content of this homogeneous mixture may be approximately the same as the lecithin phosphatide content of the mixture, but reproducibility of liposome preparation is compromised when the triglyceride is present in an excess over the phosphatide components of the lecithin used, as described in example 1.

For treatment of animals by an injection route, or for pharmaceutical (including veterinary) products generally, it may be preferable to use liposomes prepared from de-oiled lecithin from which some of the phosphatide components have been removed, for example phosphatidylinositol and phosphatidylethanolamine. In such cases, the phosphatidylcholine-enriched lecithin may be ethanol soluble and may contain a weight fraction of phosphatidylcholine in excess of 80%, or even in excess of 95%. (The highly purified lecithin in such cases is conventionally referred to as phosphatidylcholine). Such preparations may also contain no added antimicrobial agent and have antimicrobial or antiviral activity against particular pathogens by virtue of the added triglyceride. In alternative formulations, some of the high weight fraction of phosphatidylcholine may be substituted by a different purified phospholipid such as phosphatidylglycerol.

It is a particular benefit of this invention that the formulations allow for delivery of lipophilic agents within the vascular system of plants, namely the phloem and xylem, in which certain liposomes are mobile and can effect transport. This delivery allows for accumulation of active agents at sites where they can have significant benefit, for example at infected or insect-infested areas. By selecting agents with appropriate lipophilicity and aqueous solubility, liposomes can carry the agent within the vascular system with release from the liposome membrane occurring to an extent and at a rate that is tuned for optimum effect. Thus cinnamaldehyde can be delivered within the xylem in a liposomal carrier but equilibrate out of the bilayer membrane to target infectious organisms and/or across intra-plant membrane barriers and into the phloem where it is transported in "free" form to its site of action.

A sprayed application, for example by the foliar route, further allows for active delivery that is tuned by formulation adjustment to its purpose. Thus, liposomes can be prepared so as to remain resident on the leaf cuticle, or skin of a fruit, with sustained release, or residence, of an active agent. An additional benefit for certain triglyceride containing formulations is preservation of the appetizing appearance (surface color and texture) of fruit or vegetables. The prolonged residence of an active agent on a surface may be caused by prolonged adhesion to the surface of liposomes bearing the agent or by fusion, or other absorption, of the liposome membrane into a matrix of components of the surface. Alternatively the specific formulation provides a targeted delivery to sites of leaf surface infection or, via stomata, to structures and cells deeper within the leaf and the plant.

Liposomes of the present invention may be prepared to optimize delivery, to the vasculature and surrounding tissues of plants, of one or more highly colored, or preferably fluorescent, non-toxic lipophilic marker dyes. In the simplest use, this can serve for decorative purposes. In addition by employing known ratios of more than one dye in a given liposome preparation, a distinctive tracking (tagging) color or fluorescence signature can be embedded in the tissue of the living plant. Tuning of the interaction of the liposomes with the plant tissue, preferably to fuse with—or otherwise transfer the dye blend to—cell membranes in the interior of the plant provides the longest residence time within the plant. Such formulations optimized for in planta residence are of utility in marking and forensic tracking of high value specimens (for example large palm trees) that are subject to theft from commercial growers.

Direct application of essential oils to insects at various stages of development has been shown to be lethal, and such oils have also demonstrated insect repelling properties. As mentioned above, oils of these types can be formulated in liposomes that remain associated with plant (e.g. fruit and leaf) surfaces despite washing. Thus the formulations of the present invention provide a method of applying insecticidal and insect repellent natural compounds with sustained residence at the site of their desired action. Further, for volatile oils for which action in the vapor phase is significant, the liposome membrane provides a reservoir for sustained release of the vapor. This is in contrast to rapid release and diffusion away from the site of intended action when these oils are administered in other formats. Selection of oil, or combination of oils, to be used is obvious to one of ordinary skill in the art based on reports of activity of these oils in other formats.

Liposomes of the present invention provide several benefits when applying essential oils to aqueous environments: (1) dispersion in water, rather than phase separation, at concentrations above the solubility limit of the oil; (2) adhesion of liposomes to particles of decaying organic matter; (3) uptake of the liposomes by the bacteria associated with decaying organic matter. In combination, these benefits provide the further benefit of delivering relatively high (compared to "free" oils) concentrations of essential oils to filter feeding animals. In particular, the liposomes provide an effective method of delivery to filter feeding insect larvae, for example mosquito larvae. In filter feeding, the larvae consume organic particulate materials and associated bacteria (live or dead), as well as ingesting the aqueous medium—and liposomes dispersed therein—in which these materials are suspended. A further benefit is that aqueous dispersions of liposomes of a suitable size distribution allow for delivery of ovotoxic essential oils through aeropyles to the interior of insect eggs.

The following Examples are presented for illustrative purposes only, and do not limit the scope or content of the present application.

EXAMPLES

In the first series of examples, the antimicrobial activity of various liposomal formulations was studied by measuring microbial growth in a 96-well plate in the presence of varying amounts of the formulations, i.e. doses of the active agents and of the triglycerides. Absorbance was measured at 630 nm. Results are expressed as change in absorbance (from the absorbance at time t=0) measured at the time at which the control bacterial sample wells show a maximum absorbance (t=$t_{max}$). Data were not analyzed if absorbance exceeded the detector's upper useful limit of 1.8. Microbial growth inhibition (delay, reduction) or prevention was seen for the majority of the formulations tested. An alternative representation of results is as the magnitude of reduction in the growth relative to control microbial sample as measured at $t_{max}$.

In most cases, control tests using the free, i.e. non-liposomal, active agents having limited aqueous solubility, showed either unmeasurable or insignificant antimicrobial activity at the pertinent doses. For agents with significant aqueous solubility (>1 mg/ml) and a lower octanol-water partition coefficient (<100), activity was observed for the free agent that was enhanced when it was encapsulated. In the case of "control" liposomes without active agent, microbial growth was in a few cases enhanced at low triglyceride content, presumably as the liposome components provided a nutrient source for that growth. However, for some test organisms, at higher triglyceride content the liposomal triglyceride showed antimicrobial activity. This activity was dependent on the type of triglyceride, i.e. the source of the oil. Activity was enhanced by the presence of the active agent. Thus in certain cases both the liposomes themselves and the active agents separately demonstrated activity to some degree, with the combination providing an enhanced effect dependent on triglyceride content.

Liposome formulations were prepared by mixing the active agent (when selected), the relevant lecithin, triglyceride and/or plant sterol and/or lanolin together with isopropyl or ethyl alcohol to form a homogeneous single phase. Typically, heating of this mixture with stirring or high shear mixing, for example with a Polytron homogenizer, was required to generate the homogeneous single-phase mixture. This mixture was then hydrated by adding it, at about 10 wt./v %, to distilled water at a temperature of 55-60 C. The resulting hydrate was high shear mixed to produce an aqueous multilamellar vesicle dispersion that in turn was size reduced to small unilamellar vesicles (liposomes) for example by sonication or by high pressure homogenization in a piston-gap homogenizer.

Example 1: Triglyceride Content

Liposomes were prepared as described above from de-oiled lecithin (Cargill Lecigran) with varying amounts of a 1:1 mixture of olive and corn oils and citronella essential oil (Health and Beauty Natural Oils Co.—HBNOC) at 5 wt. % relative to the sum of lecithin and triglycerides (Table 1). The resulting preparations were tested at room temperature, as described, for antimicrobial activity against *Sinorhizobium meliloti*, a related and model organism for Candidatus liberibacter *asiaticus* (the citrus greening bacterium). Results are shown in FIGS. 1(a), 1(b), and 1(c) and clearly demonstrate the improvement in antimicrobial effect commencing at about 20% triglyceride content then progressively up to a triglyceride content of about 55%. It is noteworthy that at or above about this 55% level it becomes difficult to make liposomes.

TABLE 1

| Sample ID | CTRL | DOL | TG10 | TG20 | TG30 | TG40 | TG45 | TG55 |
|---|---|---|---|---|---|---|---|---|
| Wt. % triglyceride | 0 | 0 | 10 | 20 | 30 | 40 | 45 | 55 |
| Wt. % de-oiled lec. | 0 | 100 | 90 | 80 | 70 | 60 | 55 | 45 |

Example 2: Lecithin Source

The procedures of example 1 were followed for 0 wt. %, 20 wt. % and 45 wt. % triglyceride using lecithin from de-oiled soybeans, canola and sunflower. For soybean lecithin, de-oiling had been achieved by ultrafiltration (ADM Ultralec) or by acetone extraction (Cargill Lecigran). The results shown in FIG. 2(*a*) illustrate the same effect of triglyceride content although slightly altered depending on the plant source of the lecithin and the method of de-oiling. Both of these factors are expected to slightly alter the hydrophilic/hydrophobic balance profile of the liposome surfaces because of small differences in composition.

In addition, the activity of liposomes with re-oiled lecithin, prepared from de-oiled starting material (Cargill Lecigran), was compared to that of hyper-oiled liposomes prepared from crude lecithin (ADM Yelkin TS), at the same total triglyceride content and the same active agent content. The active content was 5 wt. % citronella (HBNOC), relative to the sum of lecithin and triglyceride. Although the overall triglyceride to phosphatide ratio was the same in each case, the formulations made with a de-oiled starting material exhibited higher activity as revealed in FIG. 2(*b*). This was presumably due to the influence of non-phosphatide, non-triglyceride components that slightly diminish the effective potency of the antimicrobial in the crude-lecithin based formulation.

Similar results are obtained when liposomes are formed from lecithins that have been further purified to increase the fraction of the phosphatides that is phosphatidylcholine. In these cases the shape of the curve showing dependence of activity on triglyceride content remains as seen in the results in Example 1 but the curve is shifted on the x-axis (triglyceride content). This shift results from the effect of lecithin purification on the hydrophilic/hydrophobic balance of the surface profile before addition of any triglycerides.

Example 3: Essential Oils

The procedures of example 1 were followed using a range of natural antimicrobial essential oils. A substantially similar pattern of antimicrobial effect, dependent on triglyceride content, was observed in each case. The activity, and relative potency, of some essential oils against *Sinorhizobium meliloti* is seen in FIGS. 3(*a*) and 3(*b*); overall potency against this organism generally followed the order: vetiver≈cinnamaldehyde>citronella≈sandalwood≈bayleaf≈patchouli≈rosewood>linalool≈d-limonene. Note that an antimicrobial effect (measured as inhibition of the absorbance increase at 630 nm) that is significantly greater than approximately 0.7 corresponds to a reduction in absorbance over the growth period. Such values are possibly caused by aggregation and settling of dead bacteria and values of 0.7 are considered equivalent.

Example 4: Membrane Sterol

The procedures of example 1 were followed to make liposomes containing 5 wt. % citronella and 0, 20 and 45 wt. % of the corn/olive oil mix. Additional samples were prepared in which the triglyceride was supplemented with, or fractionally replaced by, phytosterols. (Cardioaid, Cargill). Compositions are shown in Table 2. The formulations were tested as described in Example 1 and results are shown in FIGS. 4(*a*)-4(*c*). The phytosterols did not appear to have any effect on antimicrobial activity either in the absence of triglyceride or at high levels (45 wt %) of triglyceride, as seen in FIGS. 4(*a*) and 4(*b*). Notably, however, a slight enhancement of the effect of the triglyceride mixture is seen at intermediate content (20 wt. % relative to de-oiled lecithin). Either when substituted for triglyceride, or when supplementing triglyceride content, the phytosterols caused a slight increase in effect, evidenced by the consistent dip, evident especially at higher active doses, in the curves for unaltered formulation in FIG. 4(*c*). A similar effect is observed for cholesterol. In each case, the effect is presumed to occur at a sterol concentration that materially alters the hydrophilic hydrophobic balance of the surface profile of the liposomes for interaction with target entities. In the absence of triglyceride, or the presence of a large amount thereof, no material effect can be achieved.

TABLE 2

| | De-Oiled Lecithin (g) | Triglyceride, 50:50 Corn:Olive (g) | Isopropyl Alcohol (mL) | Phytosterol (g) | Citronella Java Winter (μL) |
|---|---|---|---|---|---|
| DOL | 4 | 0 | 2 | 0 | 200 |
| DOL + 15 | 4 | 0 | 2 | 0.6 | 200 |
| DOL + 30 | 4 | 0 | 2 | 1.2 | 200 |
| T620 | 3.2 | 0.8 | 2 | 0 | 200 |
| TG20 + 15 | 3.2 | 0.8 | 2 | 0.12 | 200 |
| TG20 + 30 | 3.2 | 0.8 | 2 | 0.24 | 200 |
| TG20 ± 15 | 3.2 | 0.68 | 2 | 0.12 | 200 |
| TG20 ± 30 | 3.2 | 0.56 | 2 | 0.24 | 200 |

Example 5: Lanolin

The procedures of example 1 were followed to make and test liposomes prepared from de-oiled soy lecithin (Cargill, Lecigran), and lanolin (Liquid Lanolin, Home Health Inc.) at 1, 4, 8 and 16 wt. % relative to the lecithin. The active agent was citronella (HBNOC) at 5 wt. % relative to the lecithin. The 16 wt. % lanolin preparation yielded an inhomogeneous non-liposomal mixture containing precipitate. The effects of lanolin contents between 8 and 16 wt. %, of lanolin in combination with triglyceride, and of common lanolin derivatives are also determined. FIG. 5(a) shows a strong benefit of lanolin on activity even in the absence of triglyceride.

Topical skin lotions containing sandalwood oil at 5 wt. %, lanolin at 2 wt. %, and mixed tocopherols at 0.1 wt %, relative to de-oiled lecithin, were prepared according to the method of example 1 using de-oiled lecithin (Cargill Lecigran) with isopropyl alcohol, or with ethanol in place of the isopropyl alcohol. (Preparations with alternative ratios of essential oil and lanolin were also successfully prepared, for example 3 wt % lanolin and 8 wt % sandalwood oil). The antimicrobial compounds methyl and propyl paraben were then added to the liposome dispersions at 0.1 wt %. In each case a free flowing pleasantly scented lotion was produced. It was readily absorbed by the skin on hands and face without leaving a greasy feel or residue. Addition of 2 wt % percent carboxymethylcellulose (Methocel) yielded a cream, rather than a lotion, having similar properties.

Further, a similar liposome preparation but containing less carboxymethylcellulose was used to make a shaving foam. Carboxymethylcellulose was dissolved at 0.8 wt % in the liposome dispersion (12 wt % liposome components in water); the resulting slightly thickened dispersion was poured into a typical kitchen-use dairy cream whipping device. The device was sealed and charged using a nitrous oxide cartridge. After shaking the device, the dispensing lever was depressed to produce a thick foam from the outlet nozzle. This foam was successfully used as a lather for shaving with excellent lubricity and pleasant skin sensation. (A similar result was obtained using an MLV preparation of the liposomes before size reduction). The rate of collapse of foams from size-reduced liposomes so produced with carboxymethylcellulose and with sorbitol was measured by dispensing the foam in to a graduated glass measuring cylinder and measuring the height of the column of liquid produced as the foam collapsed. FIG. 5(b) shows that foam persistence is dependent on the nature and combination of the excipient agents. It is obvious that other thickening agents may be used, with optimum concentration determined by similar collapse rate measurements.

Analogous skin lotions were prepared using lavender oil, linalool and other essential oils in place of sandalwood oil. These liposome preparations were also supplemented with mixed tocopherols as membrane components and contained preservatives such as parabens. Similar lotions are also made using topical pharmaceutical grade lecithin, or phospholipid components, for the principal component of the liposome membrane. Preservatives and buffer salts are present as needed in the external aqueous phase of the liposome dispersions. An analogous lotion, irrigation solution, or dispersion for atomizing or, with suitable thickener content, foam production, is prepared that contains curcumin and/or a lipid soluble anesthetic or pain relieving agent—such as lidocaine—in addition to an antimicrobial agent in the lecithin vesicle membrane. Such formulations are especially useful for application to compromised, burned or otherwise wounded areas of the skin of an animal. The optimum content of lanolin in such formulations is determined for each particular application.

Example 6: Quinolone Antibiotic

Figure 6:
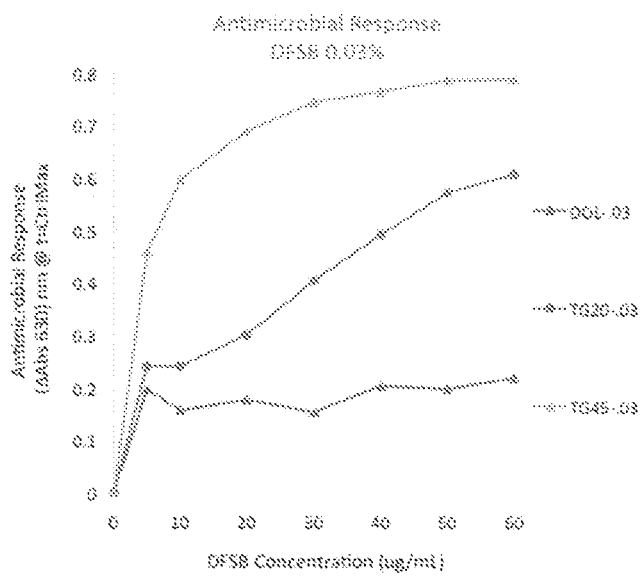
FIG. 6 is a graph showing the antimicrobial response of 0.03% DFSB antibiotic made in DOL liposomes without triglycerides (DOL shown in blue), with 20% triglycerides by weight (TG20 shown in orange), or with 45% triglycerides by weight (TG45 shown in green), according to embodiments of the present invention.
Figure 7A:
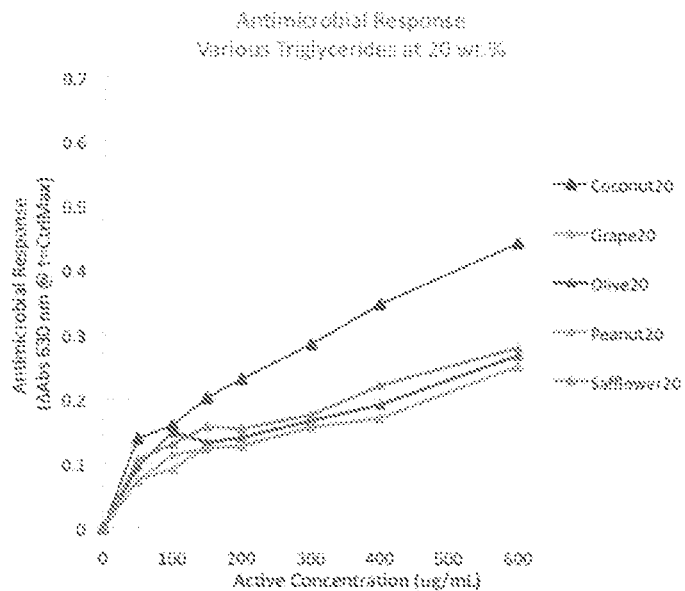
FIG. 7(a) is a graph showing the antimicrobial response of liposomes made with de-oiled lecithin and 20% triglyceride by weight from an oil selected from: coconut oil (purple), grape seed (green), olive oil (blue), peanut oil (orange), or safflower oil (brown green), as indicated, according to embodiments of the present invention.
Figure 7B:
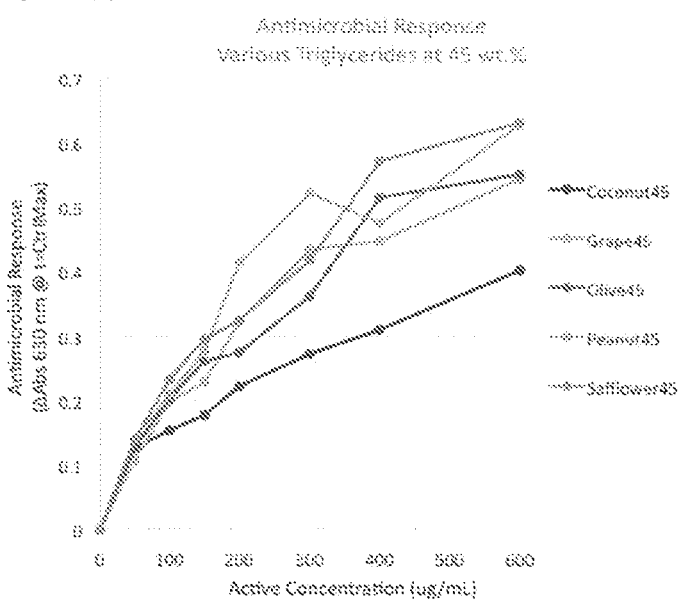
FIG. 7(b) is a graph showing the antimicrobial response of liposomes made with de-oiled lecithin and 45% triglyceride by weight from an oil selected from: coconut oil (purple), grape seed (green), olive oil (blue), peanut oil (orange), or safflower oil (brown green), as indicated, according to embodiments of the present invention.

The procedures of example 1 were followed to prepare and test the aqueous insoluble, lipophilic quinolone antibiotic DFSB (Risk Reactor, Santa Ana, Calif.) at 0.03 wt. % relative to the combined weight of de-oiled lecithin and mixed triglyceride (olive oil/corn oil) Samples were prepared with de-oiled lecithin, 20 wt. % and 45 wt. % triglyceride. Results illustrating the antimicrobial effect are presented in FIG. 6. This alternative class antibiotic was susceptible to the same activity enhancement by incorporation in liposomes, with benefit further enhanced by oiling of the liposome membrane.

Similar results are obtained for yet other common classes of antibiotics (beta-lactams, am inoglycosides, chloramphenicols, glycopeptides, oxazolidinones, sulfonamides, tetracyclines, macrolides, ansamycins, strepto gramins and lipopeptides) including by formulating water-soluble members of these antibiotic classes in the interior aqueous interior compartment of liposomes prepared with varying triglyceride contents. The pattern of results showing the enhancement of activity of antibiotics of various classes is also seen when antifungal agents of common types including macrolides, antimetabolites, azoles, allylamines, cytoskeleton agents, and echinocandins are tested, in liposomes with tailored triglyceride content, against fungal organisms.

Example 7: Triglyceride Source of Oil

The procedures of example 1 were followed to prepare and test liposomes having the compositions shown in Table 3. Note that coconut oil triglycerides have an average molecular weight that is approximately 80% that of the other plant oil triglycerides tested, by virtue of the chain length of the fatty acyl residues. Accordingly, less coconut oil was used, relative to other triglyceride sources, so that the molar ratio of triglyceride to lecithin remained approximately constant across the two series of formulations tested (crude and de-oiled lecithin).

TABLE 3

| | Triglyceride (g) | De-Oiled Lecithin (g) | Isopropyl Alcohol (mL) | Citronella Java, Winter (μL) |
|---|---|---|---|---|
| Coconut 16% | 0.64 | 3.36 | 2.0 | 200 |
| Coconut 36% | 1.44 | 2.56 | 2.0 | 200 |
| Grape 20% | 0.8 | 3.2 | 2.0 | 200 |
| Grape 45% | 1.8 | 2.2 | 2.0 | 200 |
| Olive20% | 0.8 | 3.2 | 2.0 | 200 |
| Olive 45% | 1.8 | 2.2 | 2.0 | 200 |
| Peanut 20% | 0.8 | 3.2 | 2.0 | 200 |
| Peanut 45% | 1.8 | 2.2 | 2.0 | 200 |
| Safflower 20% | 0.8 | 3.2 | 2.0 | 200 |
| Safflower 45% | 1.8 | 2.2 | 2.0 | 200 |

FIGS. 7(*a*) and 7(*b*) show the microbial inhibition effect. In general the oils, other than coconut oil, each had a very similar effect on the antimicrobial potency of the citronella. Further the dependence of the effect on overall triglyceride content was as observed in example 1 for a corn oil:olive oil 1:1 mixture. In the case of the coconut oil, for which amounts were adjusted down by 20% (to compensate for relative molecular weight), at the lower triglyceride level tested the activity was enhanced compared to the other oils whereas at higher triglyceride level activity was reduced. It is found that purified medium chain triglycerides (MCT), as commonly used in nutritional products, yield the same results.

Example 8. Other Pathogens

A formulation of lemon myrtle essential oil was prepared from the premix composition listed in Table 4 and was tested for antimicrobial activity.

TABLE 4

| De-Oiled Lecithin | 20 g |
| DFSB | 0.1 g |
| 95% Ethanol | 8 mL |
| Lemon Myrtle | 1 mL |

Initial experiments employed test tube cultures with manual measurement of turbidity at 600 nm at a limited number of time points. The impact of lemon myrtle oil on microbial growth was as shown. The target organism was *Erwinia amylovora*, a bacterium responsible for the so-called Fireblight disease in apple and pear trees; results are illustrated in FIG. 8(*a*) for 37 and 43 hours incubation. Subsequent antimicrobial testing, with lemon myrtle replaced by citronella, carvacrol, cinnamaldehyde or sandalwood oil, was conducted against a white leaf mold-performed automatically using a 96-well plate reader, as described previously. The inhibitory effects are shown in FIG. 8(*b*). The results confirm the antibacterial effects as seen in testing against *Sinorhizobium meliloti*. Microbicidal activity was also observed in in vitro testing of several essential oils against the *botrytis* infectious organism commonly responsible for strawberry spoilage. Similar activity of liposomal formulations of essential oils, modulated by triglyceride content of the membrane, is found for fungal infections such as those from *Candida* spp., *Aspergillus* spp., and *Fusarium* spp.

Example 9. Active Agent to Lecithin Ratio

Using the formulations listed in Table 5, the effect on antimicrobial potency of the content of active agent in each liposome was studied in *Sinorhizobium meliloti*. Active agent content is the ratio of active to lecithin, or to lecithin plus triglyceride, expressed as a percentage. An initial study, 9(a), reviewed the range 3-15% wt. % active. This was followed by a study, 9(b), looking at lower concentrations of active in the membrane, down to 0.125%.

TABLE 5

| | De-Oiled Lecithin (g) | Triglyceride, 50:50 Corn:Olive(g) | Isopropyl Alcohol (mL) | Citronella Java, Winter (4) |
|---|---|---|---|---|
| Example 9(a) | | | | |
| TG20 CAJ 3% | 3.2 | 0.8 | 2 | 120 |
| TG20 CAJ 6% | 3.2 | 0.8 | 2 | 240 |
| TG20 CAJ 9% | 3.2 | 0.8 | 2 | 360 |
| TG20 CAJ 12% | 3.2 | 0.8 | 2 | 480 |
| TG20 CAJ 15% | 3.2 | 0.8 | 2 | 600 |
| TG45 CAJ 3% | 2.2 | 1.8 | 2 | 120 |
| TG45 CAJ 6% | 2.2 | 1.8 | 2 | 240 |
| TG45 CAJ 9% | 2.2 | 1.8 | 2 | 360 |
| TG45 CAJ 12% | 2.2 | 1.8 | 2 | 480 |
| TG45 CAJ 15% | 2.2 | 1.8 | 2 | 600 |
| Example 9(b) | | | | |
| TG20 CAJ 0.125% | 3.2 | 0.8 | 2 | 5 |
| TG20 CAJ 0.25% | 3.2 | 0.8 | 2 | 10 |
| TG20 CAJ 0.5% | 3.2 | 0.8 | 2 | 20 |
| TG20 CAJ 1% | 3.2 | 0.8 | 2 | 40 |
| TG20 CAJ 2% | 3.2 | 0.8 | 2 | 80 |
| TG20 CAJ 4% | 3.2 | 0.8 | 2 | 160 |
| TG45 CAJ 0.125% | 2.2 | 1.8 | 2 | 5 |
| TG45 CAJ 0.25% | 2.2 | 1.8 | 2 | 10 |
| TG45 CAJ 0.5% | 2.2 | 1.8 | 2 | 20 |
| TG45 CAJ 1% | 2.2 | 1.8 | 2 | 40 |
| TG45 CAJ 2% | 2.2 | 1.8 | 2 | 80 |
| TG45 CAJ 4% | 2.2 | 1.8 | 2 | 160 |

As shown by the curves in FIGS. 9(*a*) and 9(*b*), there is significant advantage to distributing a given dose of active agent across more carrier vehicles. Given the activity of the triglycerides themselves against this pathogen, this result is anticipated as a given dose of active agent is packaged with a higher dose of the triglycerides at the lower ratios.

Example 10: Synergy and Combinations

Using cinnamaldehyde and citronella as active agents, the agents separately and in combination in the same liposomes were tested for activity against *Sinorhizobium meliloti*. Samples were prepared and tested according to the methods of example 1 with no triglyceride, 20 wt % triglyceride or 45 wt % triglyceride. As a single agent, cinnamaldehyde had greater activity than citronella, particularly notable at a 45% triglyceride content. For the high triglyceride formulations, when fractions of the cinnamaldehyde were replaced by citronella (½ and ⅔, in the same liposome) the activity of the combination did not decrease relative to cinnamaldehyde alone, rather it increased. A combined antimicrobial effect is also shown for a water-soluble antibiotic (oxytetracycline) together with triglyceride carried by liposomes, but absent any further lipophilic active agent.

Example 11: Uptake in Cuttings

Figure 10A:
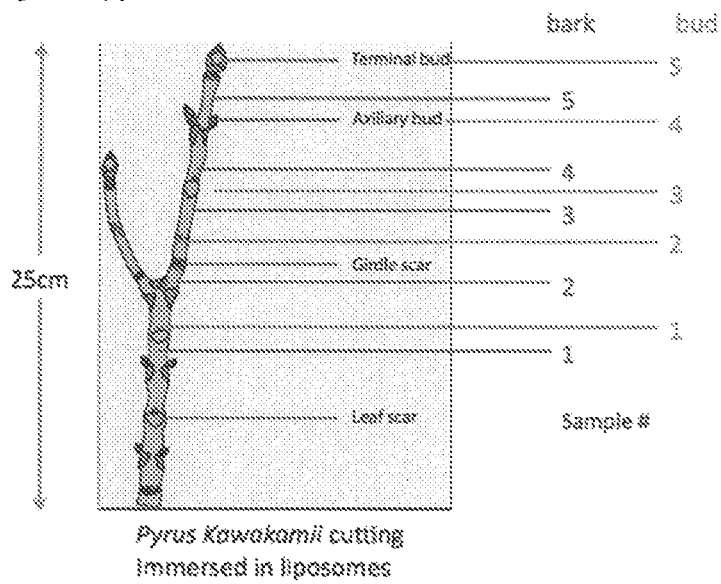
FIG. 10(a) is a schematic showing bark and bud samples 1-5 taken from a twig cutting from *Pyrus kawakamii* (ornamental pear) after the lower 3 centimeters of the twig cutting had been immersed for 48 hours in an aqueous suspension of de-oiled lecithin liposomes made with 0.005 weight % DFSB, as indicated, according to embodiments of the present invention.

A twig cutting (about 25 cm in length) was taken from *Pyrus kawakamii* (ornamental pear) and left with the lower 3 cm immersed in an aqueous suspension of liposomes prepared according to example 1 with de-oiled lecithin (Cargill) and 0.005 wt. % final DFSB. After approximately 48 hours, the cutting was removed and samples were taken as shown in FIG. 10(*a*). The samples were weighed then processed by high shear shredding with 10 ml isopropyl alcohol using a Polytron homogenizer. The homogenate was centrifuged and the supernatant recovered. The pellet was extracted two further times with isopropyl alcohol, with supernatants from all extractions pooled and brought to a total volume of 20 ml. 100 microliters of the pooled supernatant was diluted into 5 ml isopropyl alcohol and the fluorescence emission at 425 nm measured with 375 nm excitation. Relative fluorescence of the tissue samples per unit weight are listed in Table 7 and clearly show distribution through the plant vasculature, that is concentrated within the outer layers of bark, to the upper buds on the cutting. This result confirms that lipophilic, water insoluble agents can be carried by the liposomes of the present invention through the vasculature of the plant stem.

TABLE 7

| Relative Fluorescence/gram (wet weight) | | |
|---|---|---|
| Sample # | Bark | Bud |
| 1 | 4.5 | 1.0 |
| 2 | 3.3 | 4.6-5.8 |
| 3 | 1.3 | 5.1 |
| 4 | 5.5 | 4.2 |
| 5 | 1.7 | 10.2 |

Figure 10B:
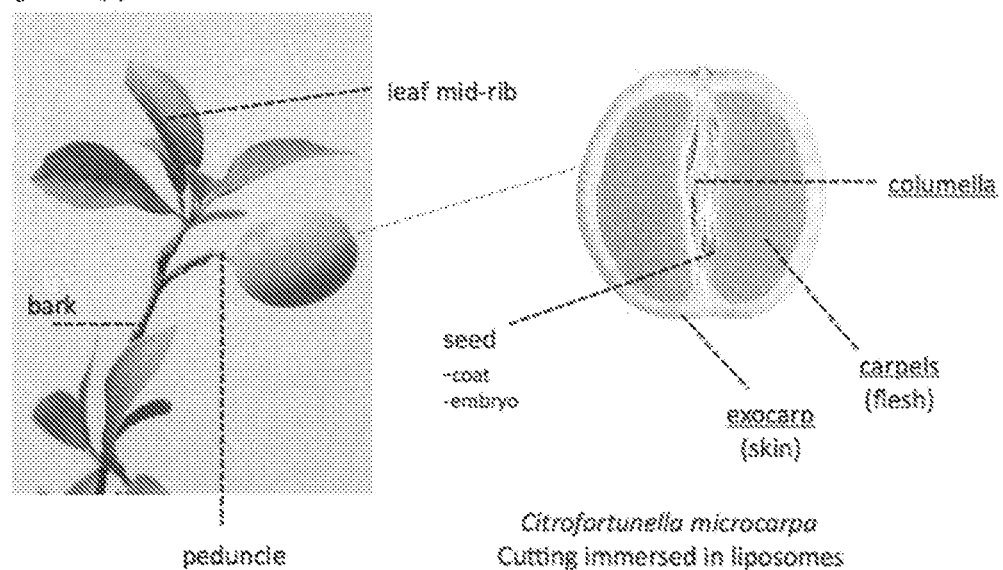
FIG. 10(b) is a schematic showing the various tissue sample cuttings taken from a *Citrofortunella microcarpa* for immersion in various liposomes formulations as set forth in Table 8, according to embodiments of the present invention.
Figure 11:
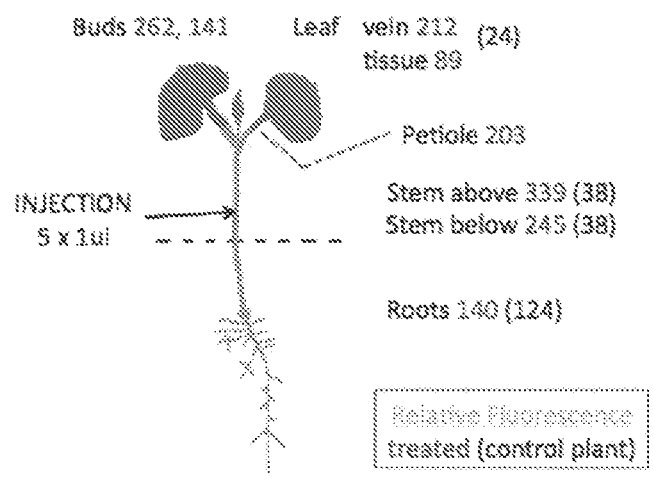
FIG. 11 is an illustration of the various portion samples and the relative fluorescence (to control plant) of *Ipomoea alba*, there were dissected 72 hours after injection with liposomal DFSB, according to some embodiments of the present invention.
Figure 12:
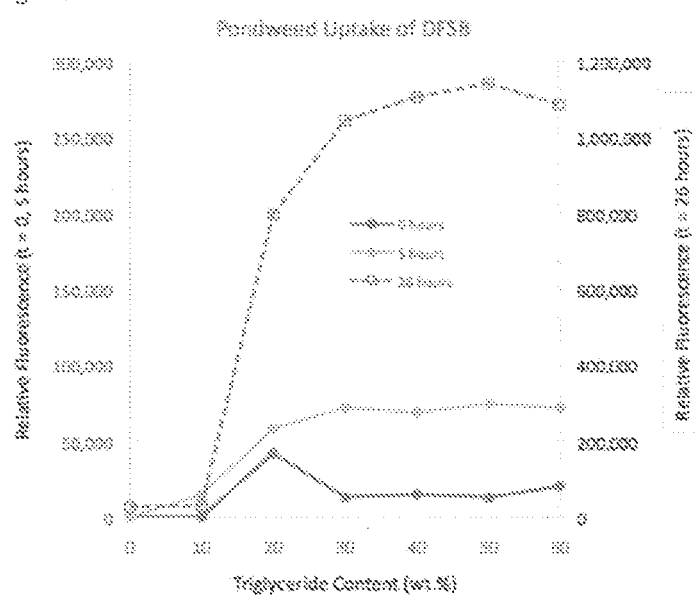
FIG. 12 is a graph showing the uptake of liposomes with DFSB, de-oiled lecithin, and varying amounts of triglyceride at 0 (blue), 5 (green), and 26 hours (open boxes), as indicated, according to embodiments of the present invention.

The experiment was repeated using cuttings from *Citrofortunella microcarpa* (Calamondin). In this case several cuttings were taken, each immersed in a different liposome formulation. The tissue samples collected were as illustrated in FIG. 10(*b*) and quantitative unit weight fluorescence values are listed in Table 8 for a liposomal composition of de-oiled lecithin with 0.005 wt. % final DFSB and citral, carvacrol or linalool as a potential natural antimicrobial agent. For comparison purposes, the fluorescence is expressed as a ratio to the fluorescence found in the leaf mid-rib for those samples taken. It is noteworthy that a high relative concentration of fluorescence in the fruit peduncle or petals was found; in infected orange trees the peduncle of the fruit is known to have disproportionately high levels of Candidatus liberibacter *asiaticus* (also known as HLB). This table also shows results from a University of Florida study that tracked in planta distribution of Candidatus liberibacter *asiaticus* in infected orange trees.

TABLE 8

| | HLB distribution | | LIPOSOME FORMULATION | | |
|---|---|---|---|---|---|
| Part of Plant | MEAN HLB cells/total DNA | +/− (SE) | Citral Rel. Fluorescence/g WET weight | Carvacrol | Linalool |
| Root | 1.54 | +/− 0.81 | | | |
| Leaf midrib | 1.00 | +/− 0.53 | 1.00 | 1.00 | 1.00 |
| Petal (flower) | 0.11 | +/− 0.07 | 3.18 | 4.69 | 2.73 |
| Pistil | 0.48 | +/− 0.23 | | | |
| Stamen | 0.18 | +/− 0.10 | | | |
| Peduncle | 10.12 | +/− 2.47 | 4.22 | 1.79 | 2.35 |
| Columella | 0.64 | +/− 0.19 | | 0.25 | 0.62 |
| Exocarp (skin) | | | | 0.05 | 0.13 |
| Seed coat | 0.38 | +/− 0.11 | | 0.35 | |
| Endosperm | 0.00 | +/− 0.00 | | 0.18 | |
| Carpels | | | | 0.05 | 0.07 |
| Young whole fruit | 0.28 | +/− 0.18 | 2.88 | | |
| Bark | 2.49 | +/− 1.02 | 2.68 | 1.01 | 0.98 |

Example 12: Injection and Distribution in Growing Seedling

In a further experiment following in planta distribution, 5×1 microliter volumes of liposomal DFSB (0.005 wt. % final), prepared as in example 1, were injected into the stem of a 10 cm high seedling of *Ipomoea alba* (Morning Glory). After 72 hours, the plant was dissected and DFSB was extracted from the various portions (illustrated in FIG. 11) using the solvent method described for plant cuttings. The figure is annotated to show the relative fluorescence of various parts of the plant and illustrate distribution of the aqueous insoluble fluorescent active agent. Comparative results fare given for background fluorescence in a control plant. Very high accumulation of fluorescent label at the buds at the tip of the plant was clearly demonstrated.

Example 13: Pondweed Uptake

Liposomes with 0.005 wt. % final DFSB, de-oiled lecithin (Cargill Lecigran), and varying proportions of triglyceride mix (olive and corn oils) were prepared according to example 1 and with the compositions indicated by the data points in FIG. 12. Approximately 1 liter of pond water was shredded by high shear blender (Polytron). 50 ml aliquots of the resulting suspension were taken, with agitation before sampling, and 5 ml of liposomal test solution was added to each of these. After 5 hours and 27 hours 5 ml samples were washed with distilled water three times (in each case spun at 3,000 g in a bench-top centrifuge to separate the pondweed from the washing solution). The final pellet was resuspended, with high shear mixing, in an extraction solution of 50% IPA and 50% acetone. The fluorescent marker was extracted and quantitated using the multiple step process described in example 11. Detection of DFSB fluorescence in the pondweed pellet confirms the association of the liposome-carried water insoluble DFSB with the aquatic organism. FIG. 12 shows the dependence of relative fluorescence on time of exposure and on the triglyceride content of the carrier vesicles.

Example 14: Microbial Uptake

The association of a fluorescent marker molecule in or from the liposome membrane with bacterial samples growing in culture broth was studied. *Sinorhizobium meliloti* bacteria were grown in culture medium for 72 hours at 25° C. in the presence of liposomes having varying triglyceride content in the membrane as listed in Table 1. The liposomes also had an inactive (no antimicrobial activity) bright yellow fluorescent marker label (diferuloylmethane) in the membrane. At the conclusion of the incubation period, the bacteria were separated by centrifuging at 2000 g for 10 minutes, washed twice with distilled water, then re-suspended in isopropyl alcohol to extract the label. After centrifuging again, the label concentration in supernatant was determined by fluorescence spectrometry. This showed a triglyceride content dependence of label uptake that largely followed the pattern of the antimicrobial activity seen in Example 1.

In a follow on microbial association study, 0.005 wt. % final DFSB was used as a fluorescent membrane label. In this case, the de-oiled lecithin. i.e. with no triglyceride, showed higher label association with the microbes than any of the triglyceride containing formulations (all of which showed similar low association). This is presumed to be because the vesicles with triglyceride modulated the DFSB's antibiotic potency and inhibited the organism growth at lower DFSB levels (and before large amounts of the fluorescent agent had associated with the cells). The de-oiled carrier, with relatively lower potency, or efficiency of delivery, is thought to have permitted more growth before an inhibitory level of the DFSB was achieved in the target. This result is consistent with association of the liposomal DFSB with microbes by an active process that is only occurring when the microbes are viable, said process being more efficient for triglyceride containing carriers for which rate and/or extent of DFSB transfer is enhanced. While the exact mechanism of transfer of the active agent to the target microbe remains undefined, herein 'rate' refers to the number of liposome:microbe interactions resulting in transfer in unit time, whereas 'extent' is used to mean fraction of DFSB content in a given liposome that transfers on each interaction (and this fraction could be 100% and/or independent of formulation).

For a water-soluble fluorescent dye entrapped in the liposomes, (% carboxyfluorescein to model a water-soluble antibiotic), the same mediation of uptake by triglyceride content is again seen. When evaluating uptake mediation by plant sterols and lanolin, the pattern of uptake enhancement is analogous to the pattern of in vitro antimicrobial activity changes seen in examples 4 and 5. Equivalent studies with other pathogens, such as those in example 8, again provide a clear correlation in pattern of uptake and antimicrobial activity, with both similarly dependent on triglyceride content. As shown in fluorescence microscopy studies, the lipophilic fluorescent molecules carried by the liposomes end up in the membrane of target cells, suggesting fusion of the liposomes with the target.

Example 15: Distribution on and Adhesion to Leaf Surfaces

*Citrofortunella microcarpa* leaves were treated with a pump aerosol spray of various liposome formulations and allowed to dry under ambient conditions. A common agricultural wetting agent (N90; polyethoxylated nonylphenyol at 1000 ppm final) was also used for all samples as an additive to the liposome formulation (after liposome preparation). DFSB at 0.005 wt. % final was included in all formulations as a lipophilic fluorescent marker. Formulations were prepared, with the compositions listed in the captions to the figures, from de-oiled lecithin with triglyceride added at levels up to 45 wt %, from crude lecithin and from crude lecithin with 3 wt % added lanolin. At various times after application, a faucet spray nozzle was used to rinse the leaf surface with domestic tap water for 30 seconds, then the leaves were allowed to dry again. Digital images of the leaves were then acquired under visible and UV light. All visible light images are essentially uninformative; however, UV illumination clearly reveals the pattern of distribution on the leaf surfaces. Image J analysis software (NIH) was used to generate the three-dimensional histogram representations of fluorescence intensity, before and after washing, following one or three hours drying, as shown in FIG. 13(*a*). These demonstrate clearly both excellent coverage and resistance to washing off. The experiment was repeated with a wider range of compositions as shown in FIGS. 13(*b*) and 13(*c*). For anomalously low leaf coverage before washing, as revealed by UV light inspection, samples were discarded. It is clear that the compositions with at least 20% triglyceride added to de-oiled lecithin in general provided excellent surface coverage that was resistant to washing off. Further, crude lecithin, despite a relatively high content of triglyceride, does not confer the same coverage or resistance although added lanolin at 3 wt % marginally improves performance.

*Pyrus kawakamii* leaves with a leaf rust infection were treated with a pump aerosol spray of a dispersion of DFSB fluorescent-labeled liposomes (de-oiled lecithin with 20% triglyceride) and allowed to dry for 48 hours under ambient conditions. Digital images of the leaves were then acquired under visible and UV light. The visible light images indicate the location of the infection and UV illumination clearly reveals the pattern of liposome distribution on the leaf surfaces. A pair of corresponding images is shown in FIG. 13(*d*); the striking co-location of liposomes with sites of infected tissue is apparent.

Example 16: Distribution on and Adhesion to Fruit Skin Surfaces

Figure 14B:
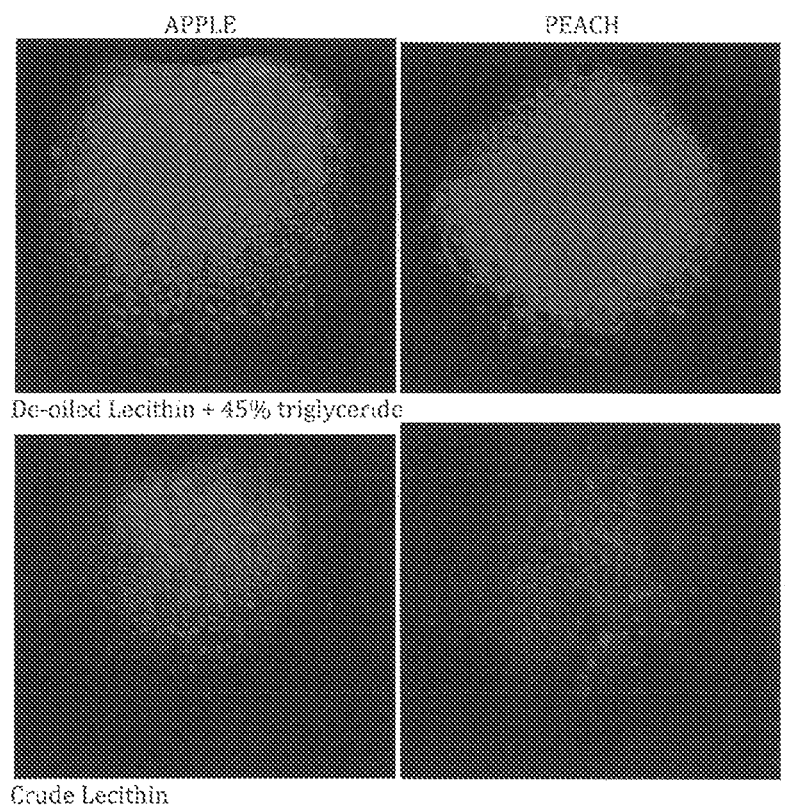
FIG. 14(b) shows UV illumination images of an apple or a peach treated with DFSB-labeled liposomes made with de-oiled lecithin with 45% triglyceride by weight or crude lecithin, as indicated, according to some embodiments of the present invention.

The DFSB-labeled preparations of Example 15 were applied by spraying onto the surface (skin) of apples, peaches, strawberries, blackberries and blueberries. Spraying typically provided a non-uniform coating, but results are illustrative of differences between formulations. The spray coating was allowed to dry for 3.5 hours, then the fruit surface was washed with tap water using a domestic faucet spray nozzle for 30 seconds. Visible and UV light images of the various fruit samples were obtained. As shown in FIG. 14(*a*) for blueberries, higher triglyceride content was associated with better coverage and resistance to washing. (All UV images shown are after washing). At 45% triglyceride added to de-oiled lecithin, and for crude lecithin, (naturally approximately 35% triglyceride), the best adhesion was found. A similar pattern was observed for the other berries, strawberry and blackberry. In contrast, for apples and peaches, while the best uniformity of coating and adhesion was found for the 45% triglyceride doping of de-oiled lecithin; the crude lecithin did not provide as good an effect as illustrated in FIG. 14(*b*). Results for these two fruits with liposomes at the 20% triglyceride level are intermediate between those shown for crude and 45% triglyceride (images not shown).

Example 17: Inhibition of Microbial Growth on Berries

Strawberries were purchased from a local supermarket and divided into groups of 25. Using a solution having *botrytis* concentration previously shown to cause development of a visible mold infection on the surface of strawberries, each group was infected by immersion for 30 seconds. After drying for 3 hours, the groups were then washed for 30 seconds (by agitating in a stainless steel mesh basket) in distilled water or in liposomal dispersions of citronella or linalool at 150 ug/ml active. Dispersions were prepared as in Example 1 with de-oiled lecithin and added 45 wt. % triglyceride; the citral or linalool was formulated at 5 wt. % relative to total lipid. Each group was allowed to air dry at ambient temperature on a raised galvanized steel mesh platform and observed for 48 hours. The development of surface botyritis infections was followed for these groups, at ambient temperature, with berries discarded when a visible infection (>1 mm$^2$) was detected at a particular time interval. FIG. 15(*a*) shows the fraction of uninfected berries remaining for the control (n=25, water washed) group and the liposome treated groups (combined n=50, 25 citral- and 25 linalool-liposomes). For treated groups, results were combined as they did not differ substantially from one another. The expanded-scale panel in FIG. 15(*b*) shows the delay in mold onset with about half the incidence of infection in the treated group vs controls at approximately 12 hours post washing.

It was further noted that, surprisingly, the appearance of the berries in the treated group remained appetizing for longer than for the control group. Vibrancy of the red color and tautness of the fruit surface were greater for treated strawberries. This effect is seen in the images of a matched pair of berries, taken after 48 hours ambient temperature exposure—FIGS. 16(*a*) and 16(*b*). The left panels show the control berry surface has become wrinkled and dull relative to the smooth, tight and bright surface of the treated berry (right panel). Using Image-J analysis software (NIH), the red channel of the digital image, top panel in FIG. 16(b), was analyzed for intensity. Results are displayed in the lower panel and quantitatively confirm the visually observed effect.

Example 18: Entomological Applications

Mosquito larvae and water were harvested from a pond. Larvae were separated with a 20 mL aliquot of pond water to which was added 40 microliters of a liposomal formulation of coriander and lavender oils (2.5 wt % of each oil relative to lecithin). The liposomes were prepared as in previous examples from de-oiled lecithin with 20 wt % corn-olive oil mixture and 0.0015 wt % final DFSB (as a fluorescent marker). The oil combination is not toxic to the larvae at the concentration used. Following five days growth, a larva was harvested, euthanized with isopropyl alcohol then repeatedly washed with distilled water before being photographed under visible and UV light. In addition, the particulate matter in 1 ml of the liposome treated suspending pond water was washed by dilution in 10 ml distilled water, centrifuging and decanting off the supernatant. This washing procedure was repeated for a total of four washes. The final precipitate was resuspended in distilled water. The images in FIG. 17 clearly show that the fluorescent label attaches to particulate matter in the pond water. As seen in FIGS. 18 (a) and (b), subsequently the label was also found distributed throughout the larva indicating that liposomes have been ingested and metabolized. This is in contrast to typical labeling studies in which dye-colored clay particles, or carbon black particles, are consumed by larvae but only label the gut compartment contents.

When the coriander-lavender oil mixture was replaced by essential oils known to have toxicity to mosquito larvae, singly or in combination, significant larval death was observed within 24-48 hours. In these experiments, larvicidal activity was found to follow the order thymol>cinnamaldehyde~d-limonene>citronella~eugenol>sandalwood oil~coriander oil~lavender oil. For thymol, cinnamaldehyde and d-limonene>50% lethality was found within 48 hours at essential oil concentrations (in pond water)<25 ppm. The co-inclusion in the liposomes, together with larvicidal essential oil, of compounds known to be essential to larval growth, such as phytosterols and omega-3 fatty acids (in particular EPA), is found to stimulate feeding rate of larvae thus enhancing toxicity of the application of the liposomes to the pond water.

While the present invention has been illustrated and described with reference to certain exemplary embodiments, those of ordinary skill in the art will understand that various modifications and changes may be made to the described embodiments without departing from the spirit and scope of the present invention, as defined in the following claims.

The invention claimed is:

1. A liposome composition having a lipid bilayer membrane, comprising:
   crude or de-oiled lecithin;
   at least one added triglyceride, wherein either a weight ratio of the added triglyceride to the de-oiled lecithin is greater than about 1:5 and less than about 1.75:1, or a weight ratio of the added triglyceride to the crude lecithin is greater than about 0.05:1;
   a non-triglyceride active agent; and
   conditioned water.

2. The liposome composition of claim 1, wherein the non-triglyceride active agent is lipophilic and is incorporated in the lipid bilayer membrane.

3. The liposome composition of claim 1, wherein the non-triglyceride active agent is membrane-impermeable and water soluble.

4. A dispersion of the liposome composition of claim 1, further comprising a surface-active agent.

5. The liposome composition of claim 1, further comprising lanolin, a lanolin derivative, a membrane-component sterol, or a non-triglyceride membrane lipid.

6. The liposome composition of claim 1, wherein the composition has a volume weighted mean diameter as measured by dynamic light scattering of less than 1 micron.

7. The liposome composition of claim 6, wherein the volume weighted mean diameter as measured by dynamic light scattering is less than 500 nm and the liposomes are predominantly unilamellar.

8. The liposome composition of claim 1, wherein the weight ratio of the added triglyceride to the de-oiled lecithin is greater than about 1:5 and less than about 1.75:1.

9. The liposome composition of claim 1, wherein the weight ratio of the added triglyceride to the crude lecithin is greater than about 0.05:1.

10. The liposome composition of claim 2, wherein the ratio of moles of any lipophilic active agent to the sum of the moles of lecithin and any added triglyceride is selected from less than 1:1, more than 2:100 and no more than 80:100, or more than 10:100 and no more than 50:100.

11. The liposome composition of claim 1, further comprising up to 15 weight % of lanolin or a lanolin derivative relative to de-oiled lecithin.

12. The liposome composition of claim 1, further comprising up to 30 weight % of a natural membrane component sterol relative to the sum of the weights of lecithin and any added triglyceride.

13. The liposome composition of claim 1, wherein the active agent is a fluorescent molecule having an excitation wavelength in the ultraviolet region of the spectrum and an emission wavelength approximately corresponding to the excitation wavelength of a chlorophyll molecule.

14. The liposome composition of claim 1, further comprising an added purified phospholipid or fatty acid.

15. The liposome composition of claim 13, wherein the liposome composition further comprises or is dispersed in an aqueous solution containing a surface active agent.

16. The liposome composition of claim 15, wherein the surface active agent is a polyoxyethylenesorbitanmonoalkylester or a polyoxyethylenealkylether.

* * * * *